US008379197B2

(12) United States Patent
Panza et al.

(10) Patent No.: US 8,379,197 B2
(45) Date of Patent: *Feb. 19, 2013

(54) SPECTROSCOPIC SYSTEMS AND METHODS FOR CLASSIFYING AND PHARMACEUTICALLY TREATING CELLS

(75) Inventors: Janice Panza, Pittsburgh, PA (US); John S. Maier, Pittsburgh, PA (US); Jason Neiss, Pittsburgh, PA (US)

(73) Assignee: ChemImage Corporation, Pittsburgh, PA (US)

( * ) Notice: Subject to any disclaimer, the term of this patent is extended or adjusted under 35 U.S.C. 154(b) by 453 days.

This patent is subject to a terminal disclaimer.

(21) Appl. No.: 12/462,350

(22) Filed: Aug. 3, 2009

(65) Prior Publication Data

US 2010/0093015 A1   Apr. 15, 2010

Related U.S. Application Data

(63) Continuation-in-part of application No. 11/650,378, filed on Jan. 5, 2007, now Pat. No. 7,570,356.

(51) Int. Cl.
 *G01J 3/00* (2006.01)
 *G01J 3/44* (2006.01)
(52) U.S. Cl. ........................................ 356/301; 356/300
(58) Field of Classification Search .......... 356/300–334, 356/402–425, 450–458
See application file for complete search history.

(56) References Cited

U.S. PATENT DOCUMENTS

| | | | |
|---|---|---|---|
| 4,661,913 A * | 4/1987 | Wu et al. | 702/19 |
| 5,539,517 A | 7/1996 | Cabib | |
| 5,866,430 A * | 2/1999 | Grow | 506/6 |
| 6,002,476 A | 12/1999 | Treado | |
| 6,040,906 A | 3/2000 | Harhay | |
| 6,048,703 A * | 4/2000 | Siman et al. | 435/7.1 |
| 6,162,604 A * | 12/2000 | Jacob | 435/6.11 |
| 6,421,553 B1 * | 7/2002 | Costa et al. | 600/476 |
| 6,950,184 B2 | 9/2005 | Stewart | |
| 7,394,546 B2 * | 7/2008 | Vakhtin et al. | 356/456 |
| 7,990,533 B2 * | 8/2011 | Maier et al. | 356/301 |
| 8,013,991 B2 * | 9/2011 | Maier et al. | 356/301 |
| 2003/0133105 A1 | 7/2003 | Gorelik et al. | |
| 2004/0053211 A1 | 3/2004 | Gradl et al. | |
| 2005/0052645 A1 | 3/2005 | Stewart | |

(Continued)

FOREIGN PATENT DOCUMENTS

WO  03060444   7/2003
WO  2005060380  7/2005

OTHER PUBLICATIONS

Koopman et al., Annexin V for Flow Cytometric Detection of Phosphatidylserine Expression on B Cells Undergoing Apoptosis, Blood, vol. 84, No. 5, 1995, pp. 1415-1420.

(Continued)

*Primary Examiner* — Gregory J Toatley
*Assistant Examiner* — Jarreas C Underwood

(57) ABSTRACT

A system and method to distinguish normal cells from cells having undergone a biochemical change. A pre-determined vector space is selected where the vector space mathematically describes a first plurality of reference spectral data sets for normal cells and a second plurality of reference spectral data sets for cells having undergone a biochemical change. A sample is irradiated to generate a target spectral data set based on photons absorbed, reflected, emitted, or scattered by the sample. The target spectral data set is transformed into a pre-determined vector space. A distribution of transformed data is analyzed in the pre-determined vector space. Based on the analysis, the sample is classified as containing normal cells, cells having undergone a biochemical change, and combinations thereof. The method includes treating the sample with a pharmaceutical agent prior to irradiating the sample and using the classification to assess the efficiency of the pharmaceutical agent.

13 Claims, 15 Drawing Sheets

U.S. PATENT DOCUMENTS

2005/0277816 A1    12/2005  Maier et al.
2006/0115804 A1*    6/2006  Hench et al. .................... 435/4
2010/0034743 A1*    2/2010  Cohen et al. .................. 424/9.1

OTHER PUBLICATIONS

Stewart et al, "A Fast Method for Detecting Cryptosporidium Parvum Oocysts in Real World Samples," Advanced Biomedicai and Clincial Diagnostic Systems III, SPIE, vol. 5692, 2005, pp. 341-350.

Maquelin et al, "Identification of Medically Relevant Microorganisms by Vibrational Spectroscopy," Journal of Microbiological Methods, Elsevier, Amsterdam, NL, vol. 51, No. 3, Nov. 1, 2--2, pp. 255-271.

Extended European Search Report, PCT/US2006029187. Nov. 24, 2009.

Supplementary European Search Report, PCT/US03/00868, Oct. 8, 2010.

Written Opinion of the International Searching Authority, PCT/US2006/029187, Aug. 26, 2008.

International Preliminary Report on Patentability, PCT/US2006/029187, Mar. 1, 2011.

* cited by examiner

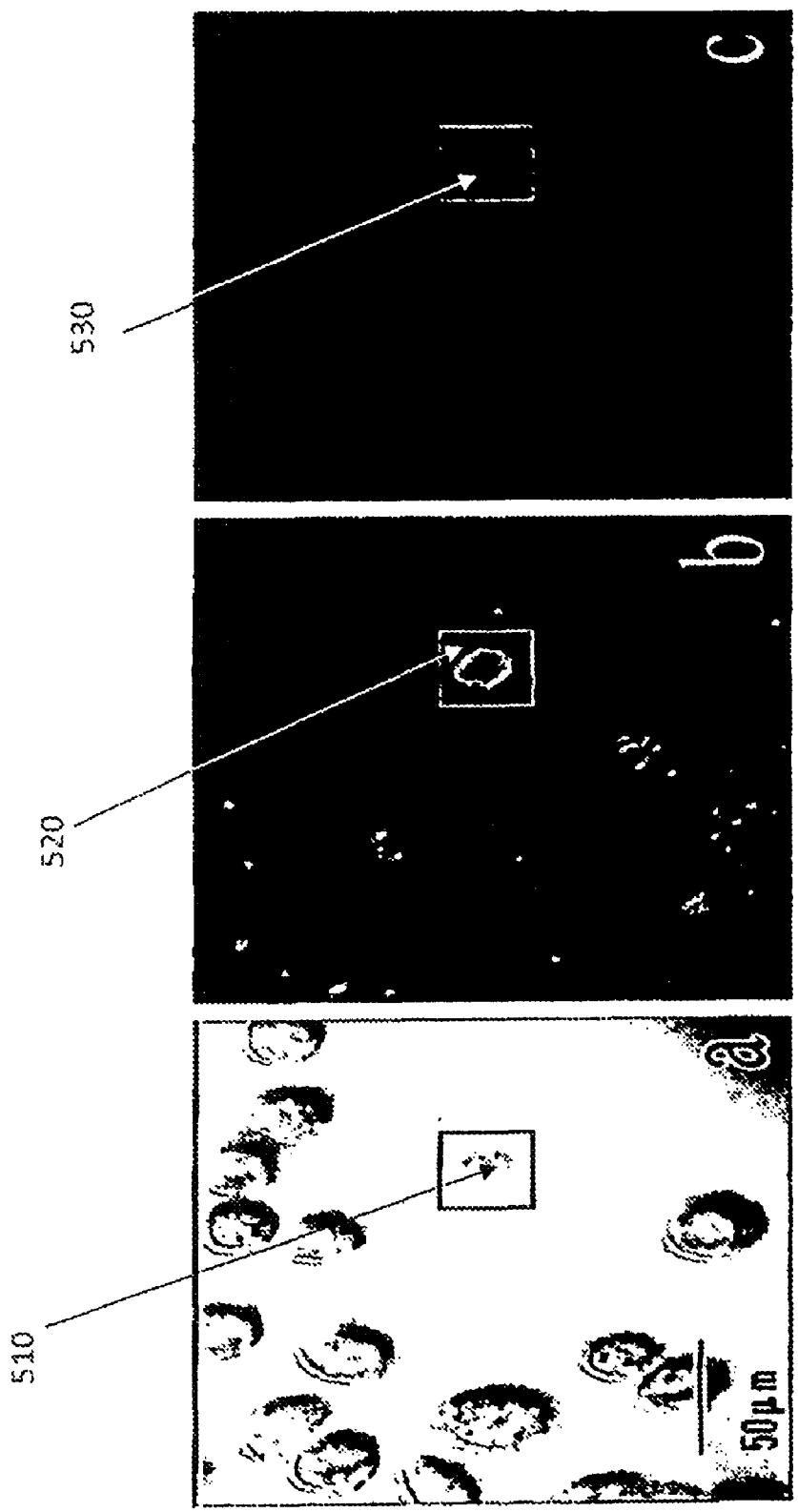

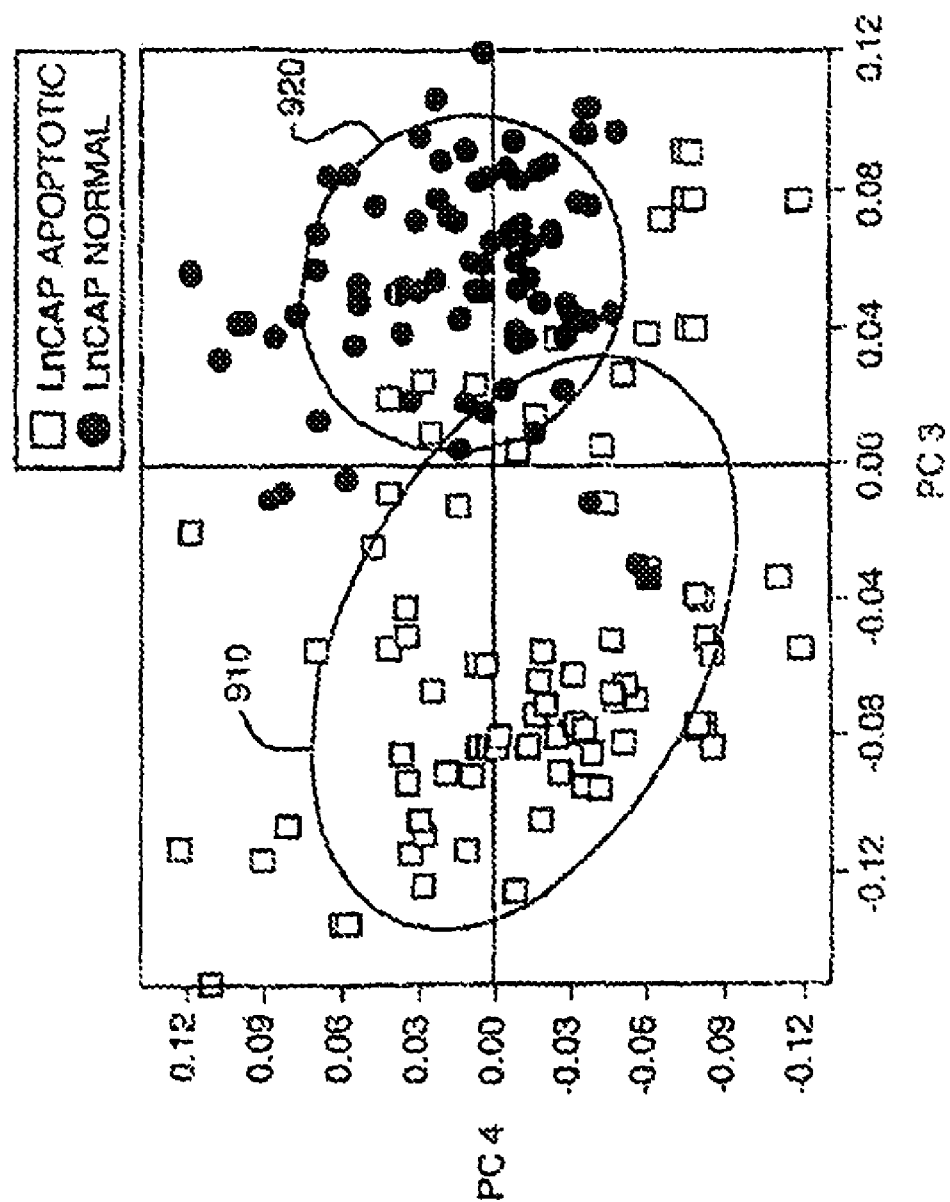

SPECTROSCOPIC SYSTEMS AND METHODS FOR CLASSIFYING AND PHARMACEUTICALLY TREATING CELLS

RELATED APPLICATIONS

This application is a continuation-in-part of U.S. application Ser. No. 11/650,378, entitled "System and Method for Classifying Cells and the Pharmaceutical Treatment of Such Cells Using Raman Spectroscopy", filed on Jan. 5, 2007, which claims the benefit of U.S. Provisional Application No. 60/756,382 entitled "Raman Molecular Imaging for Drug Development", filed Jan. 5, 2006, and U.S. Provisional Application 60/877,918 entitled "Raman Spectroscopy and Raman Chemical Imaging of Apoptotic Cells", filed Dec. 29, 2006 each of which are incorporated herein by reference in their entirety.

FIELD OF DISCLOSURE

The present disclosure relates generally to a method and system to use spectroscopic methods to identify normal and abnormal cells and thereby to study the efficiency of pharmaceutical treatment of such cells.

BACKGROUND

There are a numerous biochemical changes that may occur in a cell during its lifetime. These changes may include but are not limited to malignant transformation, gene up regulation, gene down regulation, change in receptor function, change in protein construction, change in gene transcription, and apoptosis.

Apoptosis is a cellular process wherein cells initiate a series of events that lead to their ultimate demise. Apoptosis is as important to cell life cycle regulation as growth processes such as mitosis. Normal cells use apoptosis to insure appropriate development and protect against anything that may threaten cell integrity. Abnormal cells lose the ability to properly regulate themselves through apoptosis. When there is not enough apoptosis, cells will grow out of control as demonstrated in cancerous disease states. In other diseases, cells may exhibit too much apoptosis. For example, the decline of CD4+ T cells resulting from AIDS is likely due to apoptosis.

There are three mechanisms by which cells may initiate apoptosis: intrinsic pathway, extrinsic pathway, and apoptosis inducing factor (AIF). In the intrinsic pathway, also known as the mitochondrial pathway, the apoptotic process is triggered by internal cellular signals. Conversely, the extrinsic pathway, also called the death receptor pathway, is due to an external signaling mechanism. Independent of the intrinsic and extrinsic pathways, some cells require a specific protein, AIF, to trigger apoptosis.

Regardless of the mechanism by which apoptosis occurs, there are a series of morphological changes that are detectable and considered to be the standard to define the mode of cell death. Some of the changes include cell shrinkage, cell surface blebbing, nuclear chromatin condensation, and apoptotic body formation. Typically, a trained eye, using simple techniques such as microscopy, cytometry, and imaging, detects the morphological changes.

The morphological changes of cells during the apoptotic process are due to underlying biochemical and molecular events. The biochemical and molecular events are more difficult to ascertain because they typically require complex cellular assays that are usually tedious, unreliable, or lead to results that are difficult to interpret. For example, annexin V labeling is a common cellular assay to confirm apoptosis. Apoptotic cells lose their ability to regulate the composition of their lipid membranes and phosphatidylserine (PS), which is located on the internal plasma membrane in normal cells, is externalized and expressed on the outer plasma membrane of apoptotic cells. Annexin V is a protein that binds to PS and is used as a fluorescent marker to label PS in several commercially available apoptosis assay kits. Although annexin V labeling is a current method to detect apoptosis, challenges remain in the interpretation of the results from this type of assay.

There exists a need to be able to detect the biochemical changes in cells without a reagent-based, multi-step cellular assay. The present disclosure provides such a method using Raman spectroscopy.

SUMMARY

The present disclosure provides for systems and methods to distinguish normal cells from cells having undergone a biochemical change. Throughout this disclosure, reference to normal cells may indicate reference to cells that have not undergone a biochemical change. In such an embodiment, a pre-determined vector space is selected where the vector space mathematically describes a first plurality of reference spectral data sets for normal cells and a second plurality of reference spectral data sets for cells having undergone a biochemical change. The sample is irradiated to thereby generate photons emitted, reflected, absorbed, and scattered by the sample. The photons are collected to generate a target spectral data set. The spectral data set is then transformed into the pre-determined vector space. The distribution of transformed data in the pre-determined vector space is analyzed and based on this analysis, a the sample can be classified as having at least one cell that is normal or at least one cell that has undergone a biochemical change.

In one embodiment, the first reference data set of spectra data sets is selected from the group consisting of: a plurality of first reference Raman spectra wherein each spectrum corresponds to a reference normal cell, a plurality of first reference spatially accurate wavelength resolved Raman images wherein each image corresponds to a normal cell, a plurality of first reference infrared spectra wherein each spectrum corresponds to a reference normal cell, a plurality of first reference spatially accurate wavelength resolved fluorescence spectra, a plurality of first spatially accurate wavelength resolved fluorescence images, a plurality of first reference spatially accurate wavelength resolved infrared images wherein each image corresponds to a reference normal cell, a plurality of first reference ultraviolet spectra wherein each spectrum corresponds to a reference normal cell, a plurality of first reference spatially accurate wavelength resolved ultraviolet images wherein each image corresponds to a reference normal cell, a plurality of first reference visible spectra wherein each spectrum corresponds to a reference normal cell, a plurality of first reference spatially accurate wavelength resolved visible images wherein each image corresponds to a reference normal cell, and combinations thereof.

In one embodiment, the target spectral data set is selected from the group consisting of: a plurality of Raman spectra of the sample, a plurality of spatially accurate wavelength resolved Raman images of the sample, a plurality of infrared spectra of the sample, a plurality of spatially accurate wavelength resolved infrared images of the sample, a plurality of ultraviolet spectra of the sample, a plurality of spatially accurate wavelength resolved ultraviolet images of the sample, a plurality of visible spectra of the sample, a plurality of spatially accurate wavelength resolved visible images of the sample, a plurality of fluorescence spectra, a plurality of spatially accurate wavelength resolved fluorescence images, and combinations thereof.

In another embodiment, the photons are collected via a fiber array spectral translator device. In yet another embodiment, the photons are passed through a liquid crystal tunable filter. The sample can also be treated with a pharmaceutical agent before irradiation in another embodiment. The efficiency of the treatment can be assessed based on the classification of the sample as containing a normal cell or a cell having undergone a biochemical change. In another embodiment, the treatment can also be used to cause a biological change in at least one cell and/or preventing a biological change in at least one cell in the sample.

In one embodiment, said analyzing is performed by calculating a Mahalanobis distance between the target spectral data set transformed into vector space and one or more of the following: a first plurality of reference spectral data sets in said pre-determined vector space; and a second plurality of reference spectral data sets in said pre-determined vector space.

The systems and methods of the present disclosure may be used to analyze samples to identify and classify any number of biochemical changes known in the art including but not limited to the following: apoptosis, malignant transformation, gene up regulation, gene down regulation, change in receptor function, change in protein construction, and change in gene transcription.

The present disclosure provides for method to distinguish normal cells from apoptotic cells. A pre-determined vector space is selected where the vector space mathematically describes a first plurality of reference Raman data sets for normal cells and a second plurality of reference Raman data sets for apoptotic cells. A sample is irradiated with substantially monochromatic light generating scattered photons. A target Raman data set is collected where the Raman data set is based on the scattered photons. The target Raman data set is transformed into a vector space defined by the pre-determined vector space. A distribution of transformed data is analyzed in the pre-determined vector space. Based on the analysis, the sample is classified as containing normal cells, apoptotic cells, and a combination of normal and apoptotic cells.

In one embodiment, the analysis is performed by calculating a Mahalanobis distance between the target Raman data set which has been transformed into the vector space and one or more of the following: the first plurality of reference Raman data sets in said pre-determined vector space; and the second plurality of reference Raman data sets in said predetermined vector space.

In another embodiment, the method further includes the step of treating the sample with a pharmaceutical agent prior to irradiating the sample. Based on the classification, the therapeutic efficiency of the pharmaceutical agent is assessed.

In yet another embodiment, the target Raman data set corresponds to one or more of the following: a plurality Raman spectra of the sample; and a plurality of spatially accurate wavelength resolved Raman images of the sample.

In accordance with a further aspect of the present disclosure, the first reference set of Raman data sets corresponds to one or more of the following: a plurality of first reference Raman spectra and a plurality of first reference spatially accurate wavelength resolved Raman images. Each Raman spectrum corresponds to a reference normal cell and each Raman image corresponds to a reference normal cell. The second reference set of Raman data sets corresponds to one or more of the following: a plurality of second reference Raman spectra and a plurality of second reference spatially accurate wavelength resolved Raman images. Each Raman spectrum corresponds to a reference apoptotic cell and each Raman image corresponds to a reference apoptotic cell.

In yet another embodiment, a fluorescence emission signature is obtained of a fluorescent labeled sample. It is then determined whether the sample expresses phosphatidylserine and a location of at least one cell in the sample based on the fluorescence signature of the sample. A target Raman data set is collected based on the scattered photons generated by said location.

The present disclosure also provides for a system for distinguishing normal cells from cells having undergone a biochemical change. The system can be used to identify, classify and analyze any number of biochemical changes known in the art including but not limited to the following: apoptosis, malignant transformation, gene up regulation, gene down regulation, change in receptor function, change in protein construction, and change in gene transcription.

In one embodiment of the present disclosure, the system comprises: a first data base having a first plurality of reference spectral data sets representative of normal cells; a second data base having a second plurality of reference spectral data sets representative of cells having undergone a biochemical change; an illumination source; a spectroscopic device; a machine readable program code containing executable program instructions; and a processor operatively coupled to the illumination source and the spectroscopic device, and configured to execute said machine readable program code so as to perform the following: select a pre-determined vector space that mathematically describes the first plurality of reference spectral data sets representative of normal cells and the second plurality of reference spectral data sets representative of cells having undergone a biochemical change, configure said illumination source to illuminate a biological sample with light to thereby generate photons selected from the group consisting of: photons emitted from the sample, photons reflected by the sample, photons absorbed by the sample, photons scattered by the sample, and combinations thereof; configure said spectroscopic device to collect a spectral data set based on said photons selected from the group consisting of: photons emitted from the sample, photons reflected by the sample, photons absorbed by the sample, photons scattered by the sample, and combinations thereof; transform the target Raman data set into a vector space defined by the pre-determined vector space; analyze a distribution of transformed data in the predetermined vector space; based on said analysis, classify the biological sample as comprised of one of the following: normal cells, cells having undergone a biochemical change, and combinations thereof.

In one embodiment, the system may include a liquid crystal tunable filter. In another embodiment, the system may include a fiber array spectral translator device. In another embodiment, the system may further comprise both a liquid crystal tunable filter and a fiber array spectral translator device.

The present disclosure further provides for a system for distinguishing normal cells from apoptotic cells. The system includes a first and second data base, a substantially monochromatic irradiation source, a spectroscopic device, machine readable program code containing executable program instructions and a processor. The first database contains a first plurality of reference Raman data sets for normal cells. The second database contains a second plurality of reference Raman data sets for apoptotic cells. The processor is operatively coupled to the substantially monochromatic irradiation source and the spectroscopic device. The processor is further configured to execute the machine readable program code so as to perform a series of steps.

The present disclosure further yet provides for a storage medium containing machine readable program code, which, when executed by a processor, causes the processor to perform a series of steps. A pre-determined vector space is selected where the vector space mathematically describes a first plurality of reference Raman data sets for normal cells and a second plurality of reference Raman data sets for apoptotic cells. A sample is irradiated with substantially monochromatic light generating scattered photons. A target Raman data set is collected where the Raman data set is based on the scattered photons. The target Raman data set is transformed into a vector space defined by the pre-determined vector space. A distribution of transformed data is analyzed in the pre-determined vector space. Based on the analysis, the sample is classified as containing normal cells, apoptotic cells, and a combination of normal and apoptotic cells.

BRIEF DESCRIPTION OF THE DRAWINGS

The accompanying drawings, which are included to provide further understanding of the disclosure and are incorporated in and constitute a part of this specification, illustrate embodiments of the disclosure and, together with the description, serve to explain the principles of the disclosure.

In the drawings:

FIGS. 5A, 5B and 5C illustrate images of serum starved cells;

FIG. 9 illustrates the classification model of apoptotic and normal LnCAP cells;

DETAILED DESCRIPTION OF THE DISCLOSURE

Reference will now be made in detail to the preferred embodiments of the present disclosure, examples of which are illustrated in the accompanying drawings. Wherever possible, the same reference numbers will be used throughout the drawings to refer to the same or like parts.

Figure 1:
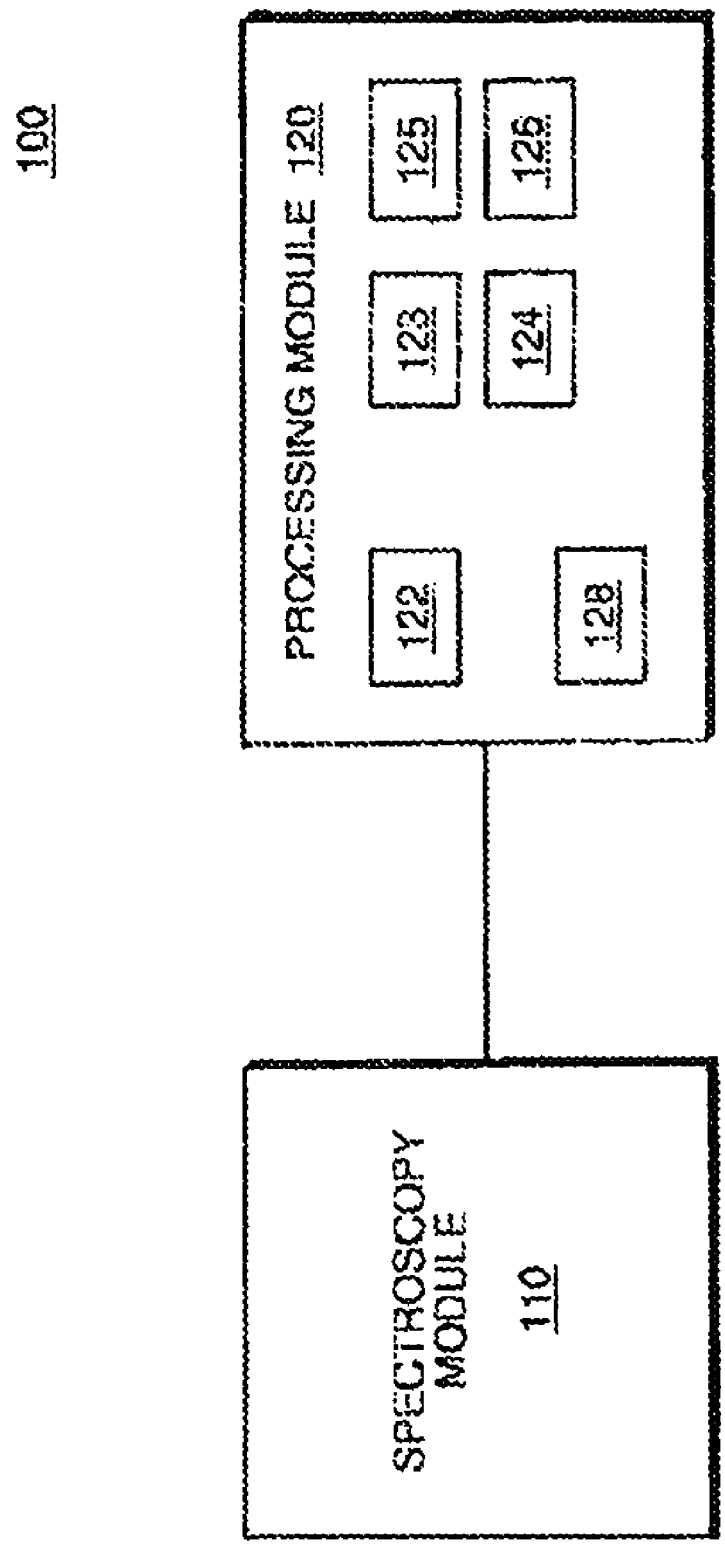
FIG. 1 schematically represents an exemplary system of the present disclosure.

FIG. 1 illustrates an exemplary system 100 of the present disclosure. System 100 includes a spectroscopy module 110 and processing module 120. Processing module 120 includes processor 122, databases 123, 124, 125 and 126, and machine readable program code 128. The machine readable program code 128 contains executable program instructions. Processor 122 is configured to execute the machine readable program code 128 so as to perform the methods of the present disclosure.

Figure 2:
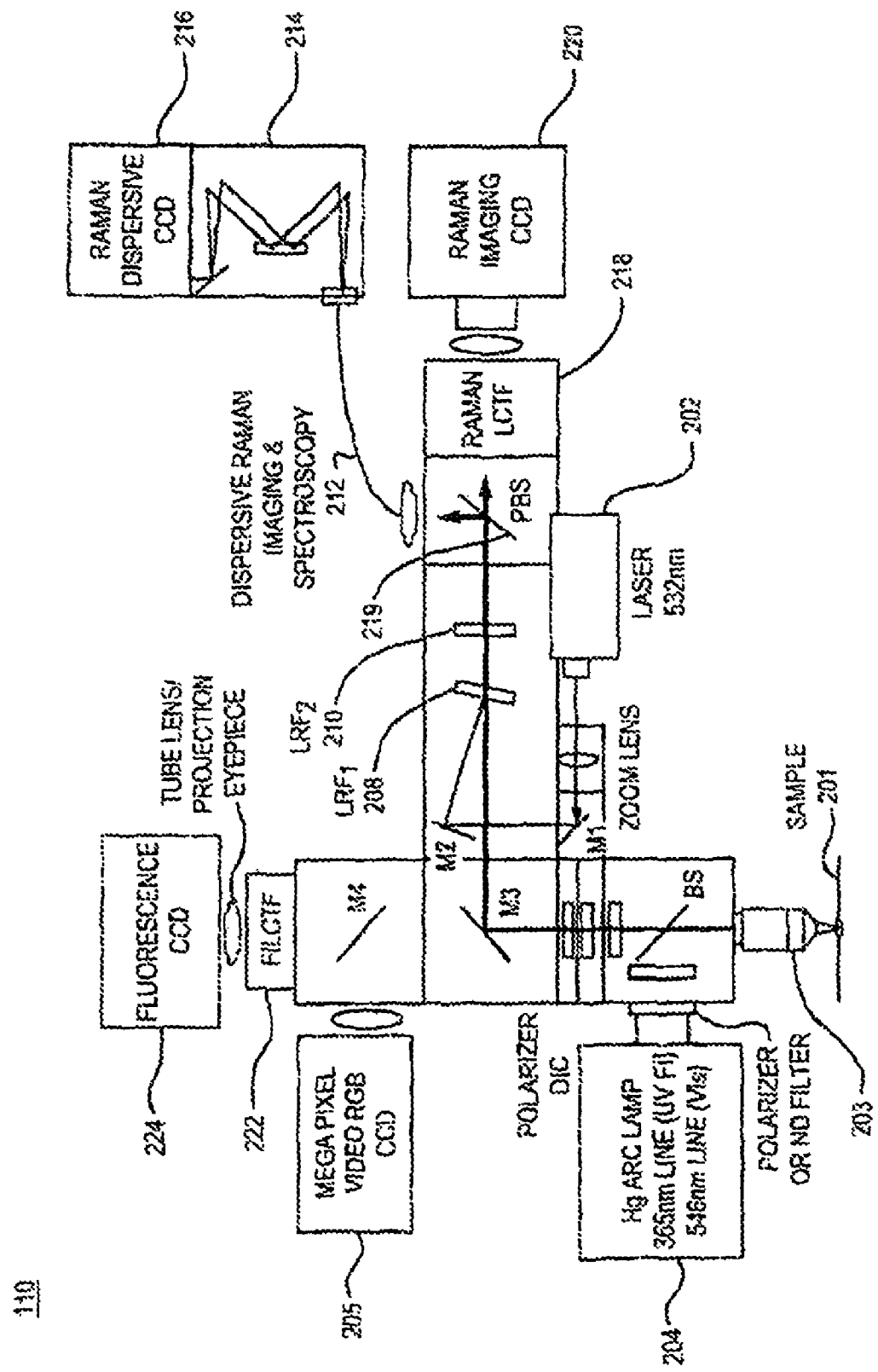
FIG. 2 schematically represents an exemplary spectroscopy module of the present disclosure.

FIG. 2 illustrates an exemplary spectroscopy module 110 of the present disclosure. Spectroscopy module 110 may operate in several experimental modes of operation including bright field reflectance and transmission imaging, polarized light imaging, differential interference contrast (DIC) imaging, UV induced autofluorescence imaging, wide field illumination whole field Raman spectroscopy, wide field spectral fluorescence imaging, and wide field spectral Raman imaging. Module 110 includes collection optics 203, light sources 202 and 204, a plurality of spectroscopic devices including fluorescence filter 222, imaging spectrometer 218 or dispersive spectrometer 214, a plurality of detectors including fluorescence detector 224, and Raman detectors 216 and 220, a fiber array spectral translator ("FAST") device 212, and filters 208 and 210. Processor 122 is operatively coupled to light sources 202 and 204, and the plurality of spectroscopic devices 214, 218 and 222. Module 110 optionally includes a video camera 205. Although not shown in FIG. 2, spectroscopy module 110 includes many additional optical and electrical components.

Sample 201 includes a variety of biological samples. In one embodiment, the sample includes at least one cell. The sample may contain normal cells, apoptotic cells or a combination of normal and apoptotic cells. In one embodiment, the cell is a mammalian cell. Representative cells includes prostate cell, kidney cell, prostate cell, lung cell, colon cell, bone marrow cell, brain cell, red blood cell, and cardiac muscle cell. In another embodiment, the cells include cells of plants, non-mammalian animals, fungi, protists, and monera.

The cells can be isolated cells, such as individual blood cells or cells of a solid tissue that have been separated from other cells of the tissue (e.g., by degradation of the intracellular matrix). The cells can also be cells present in a mass, such as a bacterial colony grown on a semi-solid medium or an intact or physically disrupted tissue. By way of example, blood drawn from a human can be smeared on the surface of a suitable Raman scattering substrate (e.g., an aluminum-coated glass slide) and individual cells in the sample can be separately imaged by light microscopy and Raman scattering analysis. Similarly a slice of a solid tissue (e.g., a piece of fresh tissue or a paraffin-embedded thin section of a tissue) can be imaged on a suitable surface.

The cells can be cells obtained from a subject (e.g., cells obtained from a human blood or urine sample, tissue biopsy, or surgical procedure). Cells can also be studied where they naturally occur, such as cells in an accessible location, cells in a remote location using a suitable probe, or by revealing cells (e.g., surgically) that are not normally accessible.

Referring to FIG. 2, light source 202 is used to irradiate sample 201 with substantially monochromatic light. Light source 202 can include any conventional photon source, including laser, LED, and other IR or near IR devices. The substantially monochromatic radiation reaching sample 201 illuminates the sample 201 producing scattered photons. In one embodiment, light source 202 includes a laser light source producing light at 532.1 nm. Filters 208 and 210 reject light at the wavelength of laser light source 202. The monochromatic light reaching sample 201 illuminates the sample and photons are scattered from different locations on or within the sample. The Raman scattered photons are collected by collection optics 203 and directed to dispersive spectrometer 214 or imaging spectrometer 218.

Spectroscopy module 110 may also include light source 204. Light source 204 is used to irradiate sample 201 with ultraviolet light or visible light. In one embodiment, light source 204 includes a mercury arc lamp. In another embodiment, light source 204 produces ultraviolet radiation ("UVA") having wavelength at 365 nm. In yet another embodiment, light source 302 produces visible light at 546 nm.

Referring to FIG. 2, dispersive spectrometer 214 and imaging spectrometer 218 function to produce target Raman data sets of sample 201. A target Raman data set corresponds to one or more of the following: a plurality of Raman spectra of the sample; and a plurality of spatially accurate wavelength resolved Raman images of the sample. In one embodiment, the plurality of Raman spectra is generated by dispersive spectral measurements of single cells. In this embodiment, the illumination of the individual cell covers the entire area of the cell so the dispersive Raman spectrum is an integrated measure of all the locations within the cell.

Figure 3A:
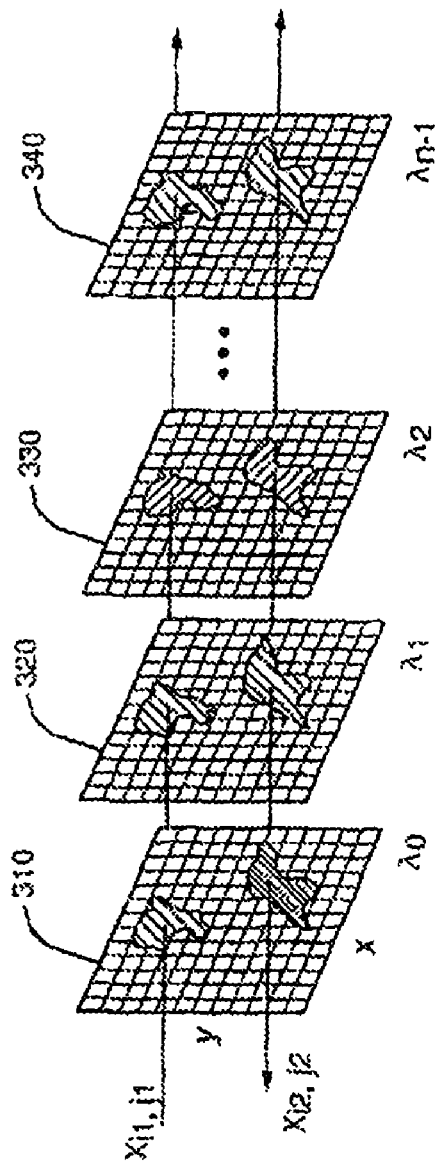
FIGS. 3A-3C illustrate a Raman data set of one embodiment.
Figure 3C:
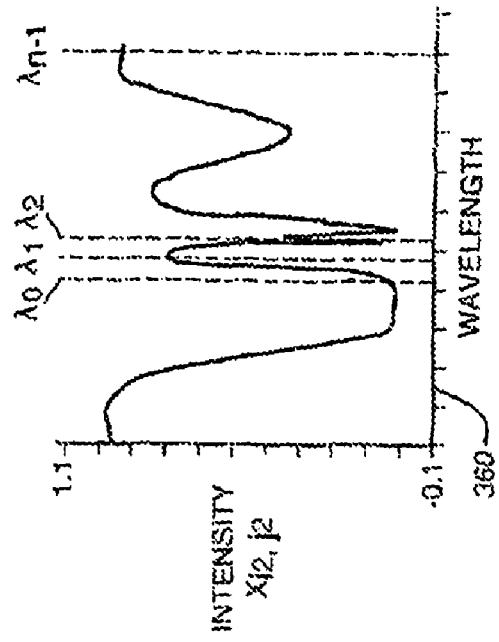
Figure 3B:
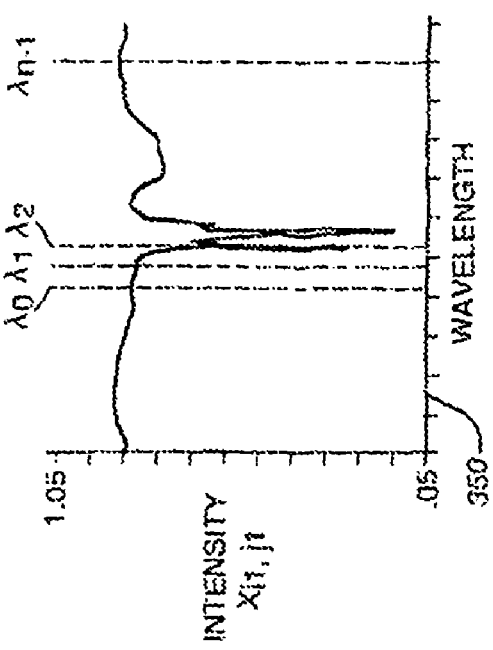

In another embodiment, the target Raman data set corresponds to a three dimensional block of Raman data, a hypercube, having spatial dimensional in the x and y dimensions and wavelength in the z dimension. In this embodiment, the plurality of Raman spectra and the plurality of spatially accurate wavelength resolved Raman images are generated, as components of the hypercube, by an imaging spectrometer 218 or the FAST device 212 in combination with dispersive spectrometer 214. FIG. 3A illustrates spatially accurate wavelength resolved images, 310, 320, 330, 340, observed at wavelengths $\lambda_0$, $\lambda_1$, $\lambda_2$ and $\lambda_{n-1}$, respectively. Each wavelength resolved image has a plurality of pixels. Each pixel has an intensity value for the amount light scattered, at wavelength $\lambda$, by the sample at the x, y position of the image. A Raman spectrum may be generated, from the plurality of spatially accurate wavelength resolved images, by extracting intensity values, for one or more pixels, for each spatially accurate wavelength resolved image in the hypercube. As illustrated in FIGS. 3A-3B, spectrum 350 is generated by extracting intensity values for the pixel located at position $X_{i1,y1}$ for each spatially accurate wavelength resolved image, 310, 320, 330, and 340, in the hypercube. In this embodiment, spectral information for each pixel of the image and is not an integrated measure of all the locations within the sample.

With further reference to FIG. 2, fluorescence filter 222 functions to produce fluorescence data sets of the sample 201. In one embodiment, the fluorescence data set includes a plurality of fluorescence spectra of sample 201 and a plurality of spatially accurate wavelength resolved fluorescence images of sample 201. A fluorescence spectrum of sample 210 contains a fluorescence emission signature of sample 201. In one embodiment, the emission signature is indicative of the fluorescent probe fluorescein isothiocyanate. The fluorescence data sets are detected by fluorescence CCD detector 224.

Figure 4B:
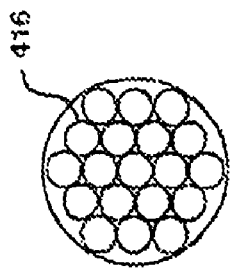
FIGS. 4A and 4B illustrate a device used in a system of the present disclosure.
Figure 4A:
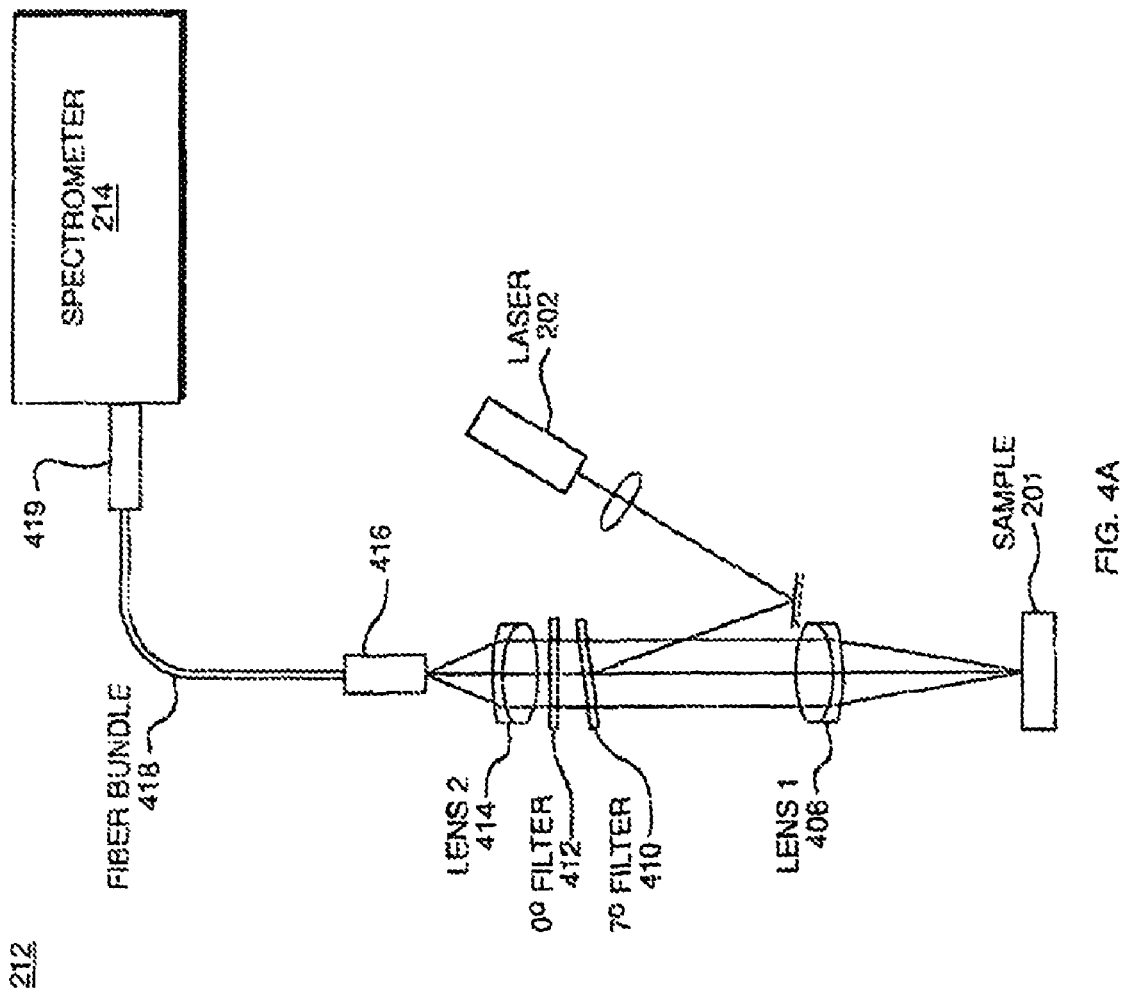

FIGS. 4A and 4B illustrate the components of a FAST device 212 which receives the collected scattered photons. With reference to FIG. 3A, the FAST device 212 includes a first lens 406, a first filter 410, a second filter 412 a second lens 414, a first end of a fiber bundle 416 and a second end of the fiber bundle 418 which is connected to a spectrometer 214. The first lens 406 acts as a collecting lens which focuses the illumination source onto the sample 201 and collects scattered photons. Photons transmitted or reflected by the sample will have the same wavelength as the laser and will be blocked by filter element 412. Lens 406 collimates the photons produced by the sample projecting the photons into infinity. The second lens 414 is used in combination with the first lens 406 to form images at the final focal plane of the second lens 414. In FIG. 3B, the first end of the fiber bundle 416 is comprised of a two dimensional non-linear array of fiber bundles. In FIG. 3A, the second end of the fiber bundle 418 is comprised of a curvilinear array of fiber bundles wherein curvilinear may include a straight line as well as a curved line configurations. The fiber array spectral translator device 212 may have as few as six fibers providing rough spatial resolution within the sample. In another embodiment, fiber array spectral translator device 212 may have 17 collection fibers providing rough spatial resolution within the sample. Alternatively, high spatial resolution could be achieved using as many as 30,000 individual fibers.

Referring to FIG. 4A, spectrograph 214 is coupled to the fiber array spectral translator device 212 and the second end of fiber bundle 318. The entrance slit of the spectrograph 214 is optically coupled to the device 212 to disperse the Raman scattered photons and to generate a plurality of spatially resolved Raman spectra.

Referring again to FIG. 2, fluorescence filter 222 and imaging spectrometer 218 are used to generate the plurality of spatially accurate wavelength resolved spectroscopic fluorescence images and Raman images, respectively. Fluorescence filter 222 and imaging spectrometer 218 include a two-dimensional tunable filter, such as electro-optical tunable filters, liquid crystal tunable filter ("LCTF") or acousto-optical tunable filter ("AOTF"). The electro-optical filter (interchangeably, tunable filters) sequentially passes emitted photons or Raman scattered photons into a plurality of predetermined wavelength bands. The plurality of predetermined wavelength bands include specific wavelengths or ranges of wavelengths. In one embodiment, the predetermined wavelength bands include wavelengths characteristic of the sample undergoing analysis. The wavelengths that can be passed through fluorescence filter 222 and imaging spectrometer 218 may range from 200 nm (ultraviolet) to 2000 nm (i.e., the far infrared). The choice of tunable filter depends on the desired optical region and/or the nature of the sample being analyzed. The two-dimensional tunable filter includes a Fabry Perot angle tuned filter, an acousto-optic tunable filter, a liquid crystal tunable filter, a Lyot filter, an Evans split element liquid crystal tunable filter, a Sole liquid crystal tunable filter, a spectral diversity filter, a photonic crystal filter, a fixed wavelength Fabry Perot tunable filter, an air-tuned Fabry Perot tunable filter, a mechanically-tuned Fabry Perot tunable filter, a liquid crystal Fabry Perot tunable filter. The tunable filer is selected to operate in one or more of the following spectral ranges: the ultraviolet (UV), visible and near infrared.

Referring to FIG. 2, the fluorescence data sets are detected by detector 224 and the Raman data sets are detected by detectors 216 and 220. Detector 224 detects, in a spatially accurate manner, the emitted photons passed by fluorescence spectrometer 222. Detector 220 detects, in a spatially accurate manner, the Raman scattered photons passed by imaging spectrometer 218. Detector 216 detects, in a spatially accurate manner, the Raman scattered photons dispersed by dispersive spectrometer 214. Detectors 216, 220 and 224 may include a digital device such as for example an image focal plane array ("FPA") or CCD or CMOS sensor. Detectors 216, 220 and 224 measure the intensity of scattered, transmitted or reflected light incident upon at multiple discrete locations, or pixels, and transfers the information received to processor module 120 for storage and analysis. The optical region employed to characterize the sample of interest governs the choice of two-dimensional array detector. For example, a two-dimensional array of silicon charge-coupled device ("CCD") detection elements can be employed with visible wavelength emitted photons or Raman scatter photons, while gallium arsenide (GaAs) and gallium indium arsenide (GaInAs) FPA detectors can be employed for image analyses at near infrared wavelengths. The choice of such devices depends on the type of sample being analyzed.

Referring again to FIG. 1, processing module 120 includes databases 123, 124, 125 and 126. The target Raman data sets and fluorescence data sets of sample 201 are stored in database 123 of processing module 120.

Processing module 120 also includes database 124 for storing a first plurality of reference Raman data sets for normal cells. In one embodiment, the first reference set of Raman data sets includes a plurality of first reference Raman spectra. Each Raman spectrum corresponds to a reference normal cell. In one embodiment, the first reference Raman spectrum corresponds to a dispersive Raman spectrum. In another embodiment, the first reference set of Raman data sets includes a plurality of first reference spatially accurate wavelength resolved Raman images. Each Raman image corresponds to a reference normal cell.

Processing module 120 further includes database 125 for storing a second plurality of reference Raman data sets for apoptotic cells. In one embodiment, the second reference set of Raman data sets includes a plurality of first reference Raman spectra. Each Raman spectrum corresponds to a reference apoptotic cell. In one embodiment, the second reference Raman spectrum corresponds to a dispersive Raman spectrum. In another embodiment, the second reference set of Raman data sets includes a plurality of first reference spatially accurate wavelength resolved Raman images. Each Raman image corresponds to a reference apoptotic cell.

In one embodiment, the first and second plurality of reference Raman data sets are generated from a three dimensional block of reference Raman data containing a plurality of reference Raman spectra and a plurality of spatially accurate wavelength resolved reference Raman images. As illustrated in FIGS. 3A-3C, and discussed above, a plurality of reference Raman spectra may be generated, from the plurality of spatially accurate wavelength resolved reference Raman images, by extracting intensity values, for one or more pixels, for each spatially accurate wavelength resolved image in the hypercube.

For example, a reference Raman data set is obtained where the data set is a hypercube including a plurality of wavelength resolved Raman images in the z direction where the images have spatial dimensional in the x and y dimensions. Each reference Raman image also has a plurality of pixels where each has a corresponding x and y position in a reference Raman image. The reference Raman data set may have one or more regions of interest having one or more apoptotic cells. The regions of interest may be identified by the size and shape of a cell in bright field imaging or by fluorescence tags. A plurality of pixels is selected where the pixels are located within the regions of interest. A single reference Raman spectrum is then extracted from each pixel located in the region of interest, leading to a plurality of reference Raman spectra for each of the regions of interest. The extracted plurality of reference Raman spectra are then designated as the reference Raman data set.

Database 126 stores a plurality of known fluorescence data sets. The plurality of known fluorescence data sets includes one or more of a plurality of fluorescence spectra corresponding to fluorescent probe molecules indicative of normal cells or apoptotic cells and a plurality of spatially accurate wavelength resolved fluorescence spectroscopic images corresponding to fluorescent probe molecules indicative of normal cells or apoptotic cells. In one embodiment, the fluorescent probe includes fluorescein isothiocyanate.

Using techniques well know to those of skill in the art, principal component analysis may be used to analyze the reference Raman data sets and the target Raman data sets. The analysis results in a classification model which is a set of mathematical vectors defined based on established methods used in multivariate analysis. The vectors form an orthogonal basis, meaning that they are linearly independent vectors. The vectors are determined based on a set of input data by first choosing a vector which describes the most variance within the input data. This first "principal component" or PC is subtracted from each of the members of the input set. The input set after this subtraction is then evaluated in the same fashion (a vector describing the most variance in this set is determined and subtracted) to yield a second vector—the second principal component. The process is iterated until either a chosen number of linearly independent vectors (PCs) are determined, or a chosen amount of the variance within the input data is accounted for. In other embodiments, the data may be analyzed using Linear Discriminate Analysis and Minimum Noise Fraction Analysis.

Mahalanobis distance algorithm may be used to calculate the distance between the pre-determined vector space and the vector space for normal cells and for apoptotic cells. The Mahalanobis distance is an established measure of the distance between two sets of points in a multidimensional space that takes into account both the distance between the centers of two groups, but also the spread around each centroid. A Mahalanobis distance model of the data is represented by plots of the distribution of the spectra in the principal component space. The Mahalanobis distance calculation is a general approach to calculating the distance between a single point and a group of points. It is useful because rather than taking the simple distance between the single point and the mean of the group of points, Mahalanobis distance takes into account the distribution of the points in space as part of the distance calculation. The Mahalanobis distance is calculated using the distances between the points in all dimensions of the principal component space.

Once the target Raman data is transformed into the space defined by the predetermined PC vector space, the target data is analyzed relative to the predetermined vector space. In one embodiment, the analysis is determined by calculating the Mahalanobis distance between the vector space of the transformed target Raman data and the predetermined vector space. The sample is classified as a normal cell, an apoptotic cell or a combination of cells based on the results of this analysis.

Figure 14:
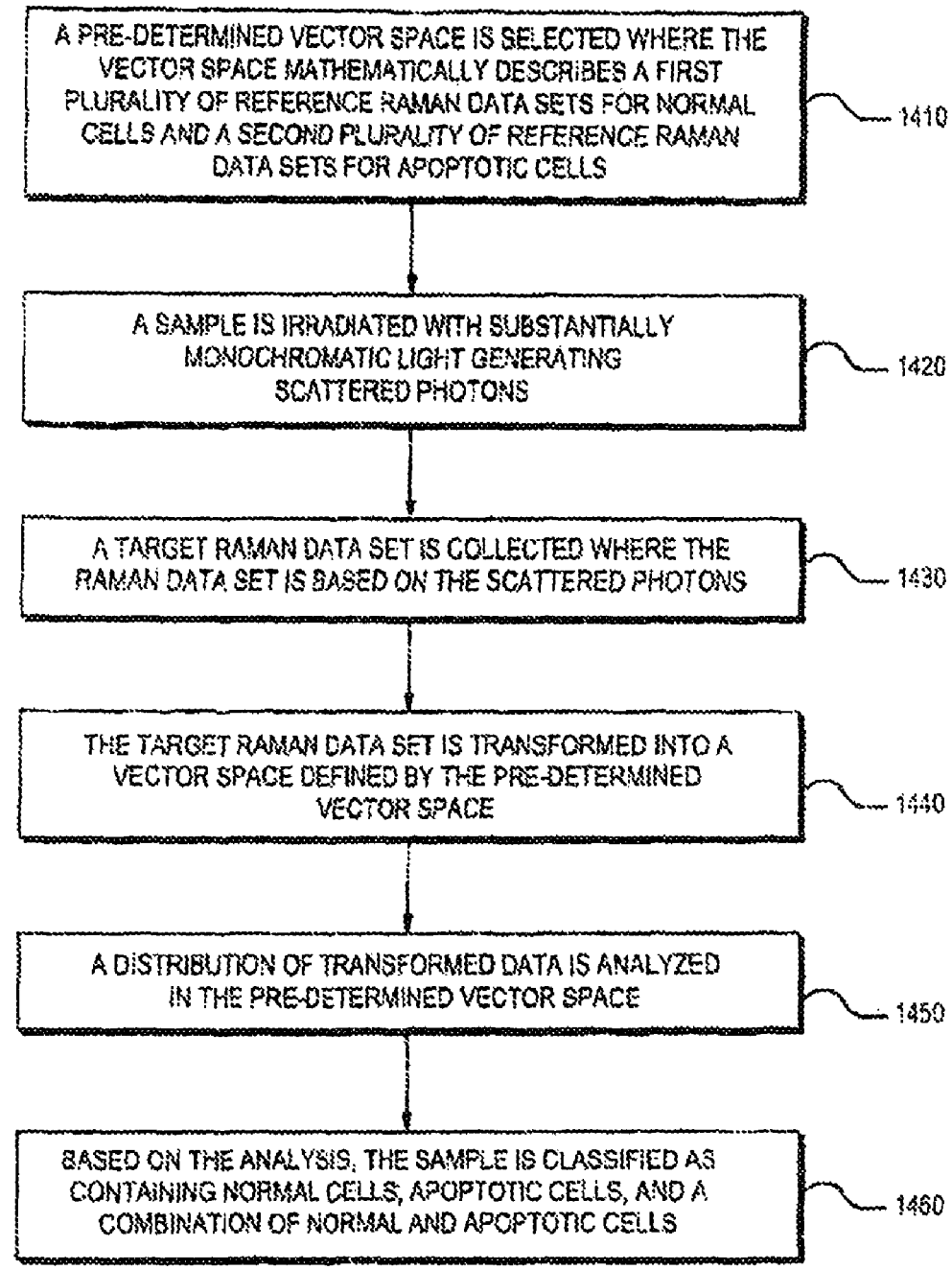
FIG. 14 is a flow chart illustrating an exemplary method of the present disclosure.

Processor 226 is also configured to execute machine readable program code containing executable program instructions to perform a variety of functions. One embodiment is illustrated in FIG. 14 which shows a flow chart for a method of the present disclosure. In step 1410, a pre-determined vector space is selected where the vector space mathematically describes a first plurality of reference Raman data sets for normal cells and a second plurality of reference Raman data sets for apoptotic cells. In step 1420, a sample is irradiated with substantially monochromatic light generating scattered photons. In step 1430, a target Raman data set is collected where the Raman data set is based on the scattered photons. The target Raman data set is transformed into a vector space defined by the pre-determined vector space, in step 1440. In step 1450, a distribution of transformed data is analyzed in the pre-determined vector space. Based on the analysis, the sample is classified as containing normal cells, apoptotic cells, and a combination of normal and apoptotic cells, in step 1460.

Figure 15:
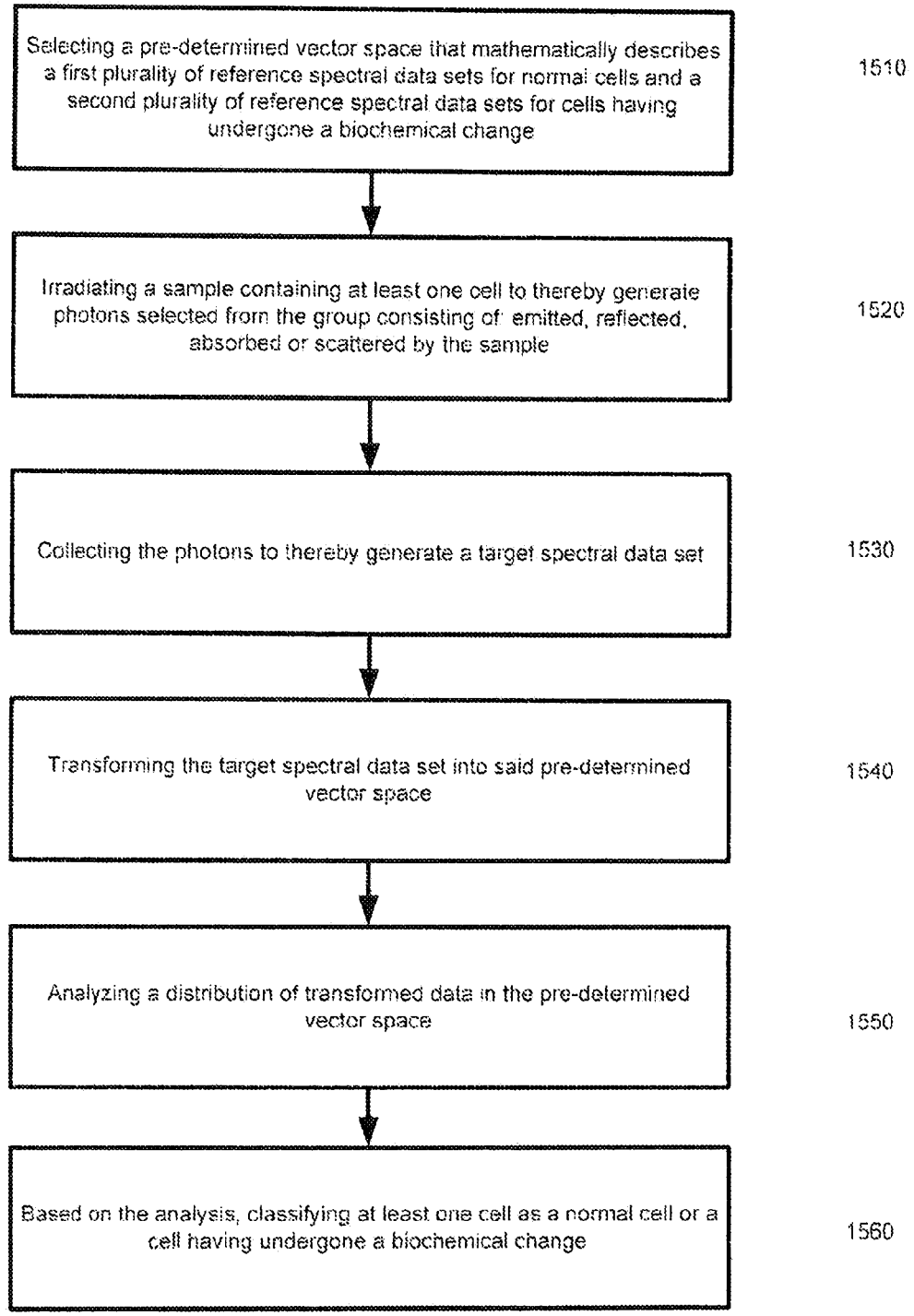
FIG. 15 is a flow chart illustrating an exemplary method of the present disclosure.

One method of the present disclosure is illustrated in FIG. 15. In step 1510, a pre-determined vector space is selected wherein the vector space mathematically describes a first plurality of reference spectral data sets for normal cells and a second plurality of reference spectral data sets for cells having undergone a biochemical change. In step 1520, the sample is irradiated to generate photons emitted, reflected, absorbed or scattered by the sample. In step 1530, the photons are collected to thereby generate a target spectral data set. The target spectral data set is transformed in step 1540 into the pre-determined vector space. In step 1550, the distribution of the transformed data is analyzed in the pre-determined vector space. Based on this analysis, the sample is classified as having at least one normal cell or one cell having undergone a biochemical change.

EXAMPLES

The following examples demonstrate the method and system of the present disclosure.

Example 1

Apoptotic cells were produced by serum starving prostrate cancer cells in culture for 24 hours. Prostate cancer cells from the PC3 cancer cell line were maintained in culture according to standard procedures. Cells were harvested using trypsin, washed, and resuspended in serum-free media. Five milliliters of the cell solution were added to a 6 well plate containing an aluminum-coated piece of glass herein referred to as a "chit". The cells were incubated for 24 hours at 37° C. After 24 hours, the supernatant was removed, and 5 ml of fresh media containing serum was added. The cells were incubated for 4 hours at 37° C. The aluminum-coated chits were removed from the 6 well plates and washed 3 times with PBS. The chits were then incubated in 5 ml 0.5% paraformaldehyde solution for 15 minutes. The paraformaldehyde solution was removed, and the chits were then incubated in 5 ml ice-cold PBS and 15 ml ice cold 90% methanol for 15 minutes. The chits were then washed 3 times with $H_2O$ and affixed to a glass slide.

The presence of apoptotic cells was confirmed through the use of a commercial assay for apoptosis (Sigma's Annexin V-FITC Apoptosis Detection Kit) and through the observation of the morphology (size and shape) of the apoptotic cells. A main marker of apoptosis is the phospholipid phosphatidylserine found in the plasma membrane of cells. In normal, living cells, phosphatidylserine is located in the inner membrane of the lipid bilayer; whereas in apoptotic cells, phosphatidylserine is translocated to the outer surface of the plasma membrane of cells. The commercial assay for apoptosis labels the phosphatidylserine through a specific interaction between phosphatidylserine and the molecule annexin V conjugated to the fluorescent probe fluorescein isothiocyanate (FITC). The apoptosis assay was a modification of the Annexin V-FITC Apoptosis Detection Kit by Sigma. The fluorescence labeling solution was prepared by added 10 µl of propidium iodide (PI) and 5 µl annexin V-FITC in 500 µl 1× binding buffer. An aluminum-coated chit was covered with the labeling solutions and incubated for 15 minutes at room temperature in the dark. The chit was then washed with 1× binding buffer and fixed according to the above procedure.

Raman spectra were collected from cells using 595 W/cm$^2$ laser power density, 100× objective, and appropriate exposure times to get good signal to noise (typically 10-60 s). Baseline, dark current and bias corrections were applied to the acquired spectra. Spectral processing and data analysis was performed using ChemImage Expert 2.0 software. Spatially accurate wavelength resolved Raman chemical images were acquired using 514 W/cm2 laser power density, 50× objective, 8×8 binning, and 10 s exposure time over the spectral range of 600-3200 cm$^{-1}$.

FIGS. 5A-5C show a series of images of a sampling of cells that were serum-starved for 24 hours. FIG. 5A is a brightfield reflectance image of the sample of cells with emphasis on cell 510. FIG. 5B is the same sampling of cells viewed through a fluorescein filter set. Cell 520 is positive for phosphatidylserine, based on its fluorescence signal, indicating that the cell is apoptotic. Cell 520 is smaller and less distinct, confirming morphological changes that are consistent with apoptosis. FIG. 5C is the sample of cells viewed using a rhodamine filter set. Cells that strongly fluoresce red are dead cells that labeled with PI. Cell 530 and the other cells within the image did not fluoresce red indicating the cells were alive at the time of fixation.

Databases were established containing reference Raman data sets for normal PC3 cells and apoptotic PC3 cells. Using the samples of fixed cells prepared through the starvation protocol, Raman spectroscopy and imaging was performed on apoptotic PC3 cells and normal PC3 cells. A series of different experimental cells preparations were evaluated to generate reference Raman data sets where cells with and without the characteristic appearance (based on size and shape) of apoptotic cells were targeted for Raman evaluation. A typical Raman evaluation included a high signal to noise dispersive spectrum, optical images, and occasionally a Raman image. These results were collected and evaluated using principal component analysis to determine a vector space which describes the normal and apoptotic spectra and their relationship to each other. Further analysis includes calculation of the Mahalanobis distance between the points representing spectra within the vector space for normal PC3 cells and for apoptotic PC3 cells.

Figure 6:
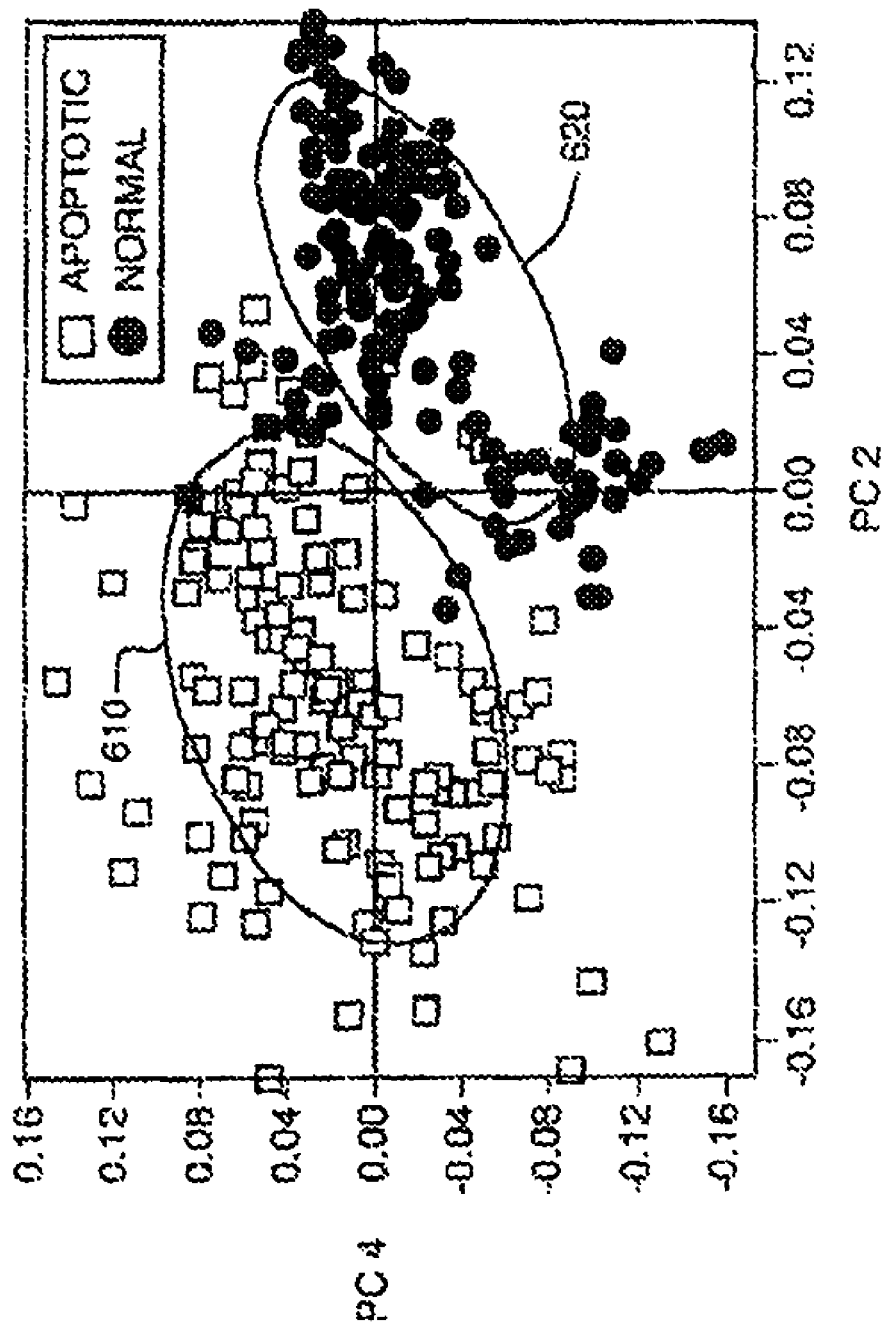
FIG. 6 illustrates the classification model of apoptotic and normal PC3 cells.

From the evaluation of reference Raman spectra from both normal and apoptotic PC3 cells by Principal component analysis, scatter plots were generated that indicate that the Raman data for normal PC3 cells and apoptotic PC3 cells in principal component space. Calculation of the Mahalanobis distance between groups in the multidimensional space leads to a quantifiable number for how separate the groups are. The fingerprint region (700-1800 cm$^{-1}$) of the Raman spectrum was used to develop the model as this region contains the relevant information necessary to distinguish the apoptotic PC3 and normal PC3 cells but does not include noise and variability of the entire spectrum. FIG. 6 illustrates the location of the measurements from apoptotic cells (610) and the normal cells (620) within the predetermined vector space. The points labeled 610 mathematically describe the reference Raman spectra data sets collected for apoptotic PC3 cells. The points labeled 620 mathematically describe the reference Raman spectra data sets collected for normal PC3 cells. The whole of FIG. 6 represents the vector space, or in this case a projection of the vector space onto the two coordinates (PC2 and PC4). These results show that apoptotic and normal cells separate in the vector space.

Although FIG. 6 shows a vector space defined by two classes, the vector space may also include background, noise class or other disease states.

Example 2

Unknown samples may be classified as normal or apoptotic based on where the sample projects into the pre-determined vector space, as illustrated in FIG. 6. The target Raman data set, obtained for the unknown PC3 cell sample, is transformed into the vector space as illustrated in FIG. 6. The vector space, for the target data, is determined from the vector dot product between the target data and each of the basis vectors or PCs. This reduces an input target measurement to a set of numbers—relative amount of each basis vector.

Figure 7:
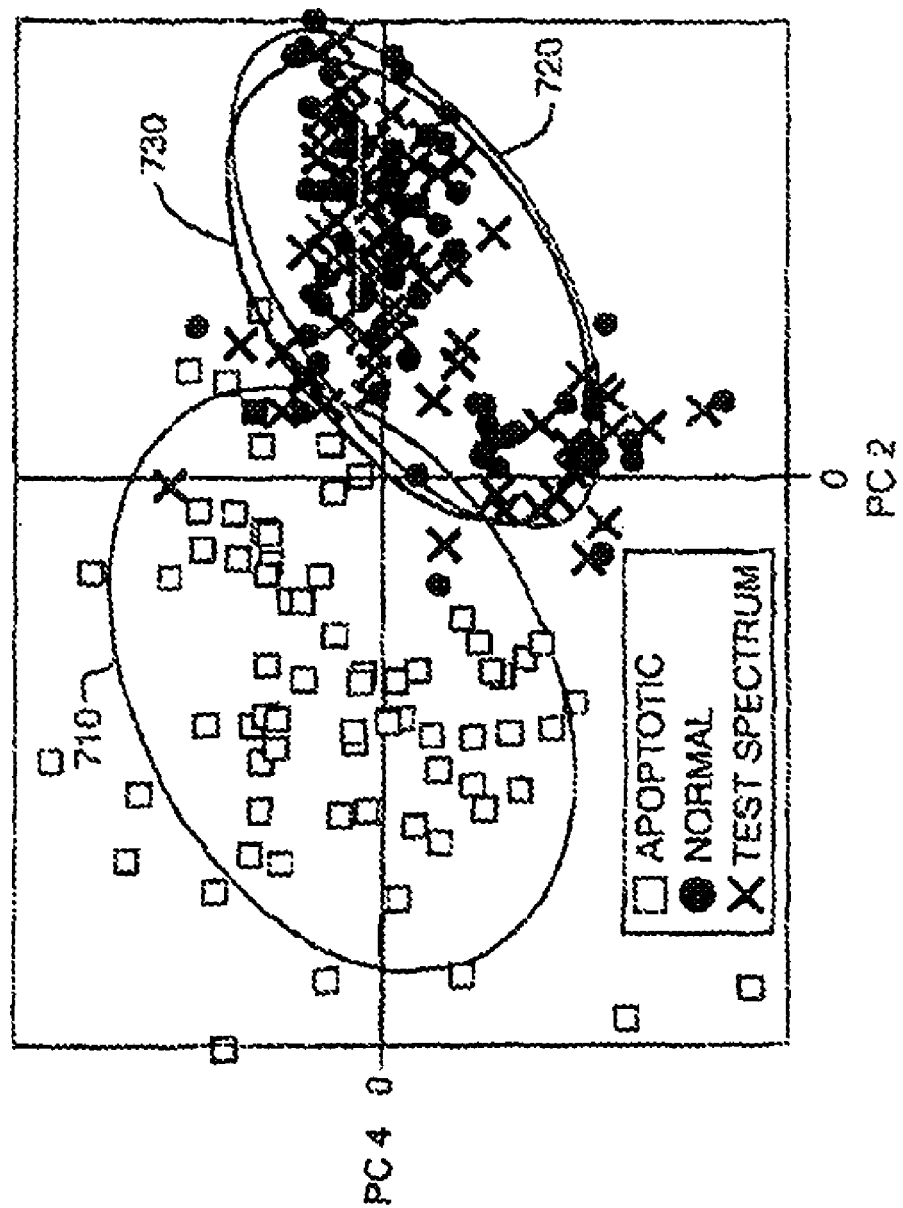
FIG. 7 illustrates projection of a Raman target data set onto the vector space of the classification model for apoptotic and normal PC3 cells.

To demonstrate the feasibility of the method of the present disclosure, half of the Raman data sets, collected for PC3 samples as described in Example 1, were used to generate a classification model. The classification model is represented by a predetermined vector space describing a plurality of reference Raman data sets for both normal PC3 cells and apoptotic PC3 cells, respectively. The second half of the Raman data sets, collected as described in Example 1, were treated as target Raman data sets for the unknown PC3 samples. The classification model and target data sets were chosen by serially selecting every other measurement independently of experimental run, day of measurement, or other experimental variables. FIG. 7 illustrates the results of this analysis. The points labeled 710 mathematically represent the reference Raman data set for apoptotic PC3 cells. The points labeled 720 mathematically represent the reference Raman data set for normal PC3 cells. The transformed data, for the target Raman data, is indicated by data points 730 marked by X. The graphical representation, shown in FIG. 7, depicts the separation of the apoptotic and normal PC3 cells in the vector space represented by the whole of FIG. 7 in this example. The statistical results, shown in Table 1, demonstrate the classification results analyzing this split sample approach.

TABLE 1

|  | Apoptotic | Normal |
| --- | --- | --- |
| Apoptotic | 141 | 16 |
| Normal | 4 | 129 |

The statistic analysis of the target Raman data, within the model, showed a sensitivity of 97.2%, a specificity of 89.0%, positive predictive value of 89.8% and a negative predictive value of 97.0%.

Example 3

Figure 8A:
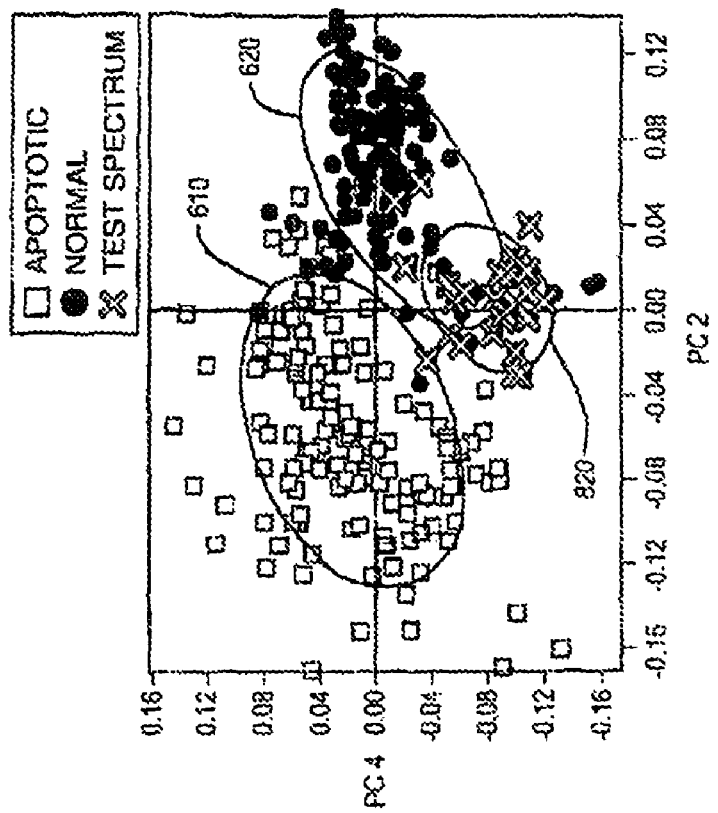
FIGS. 8A and 8B illustrate projection of a Raman target data set, based on Raman spectra, for normal and apoptotic cells onto the vector space of the classification model for apoptotic and normal PC3 cells.
Figure 8B:
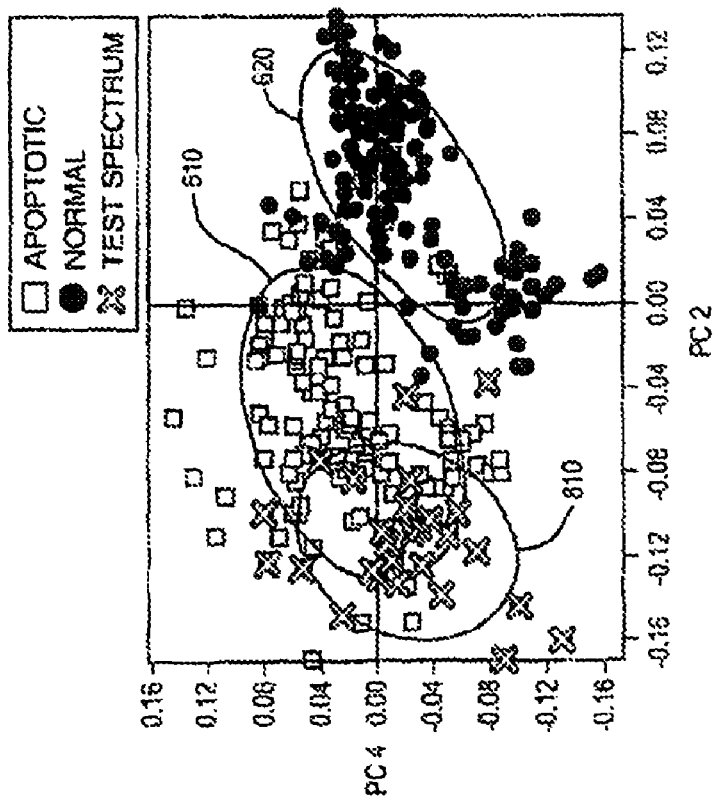

The classification model, discussed in Examples 1 and 2, was established from the reference Raman spectra of PC3 cells obtained over a series of experiments where care was taken to minimize variances between experiments. However, there will always be differences in the spectra due to instrument variability and other uncontrollable factors related to the preparation of biological samples. To test the classification model, target Raman data sets for an uncharacterized PC3 sample were collected in a single experiment. FIGS. 8A and 8B show the location of spectra from apoptotic PC3 cells 610 and normal PC3 cells 620 determined as described in Example 2. FIG. 8A, illustrates the transformed target Raman data 810 for apoptotic PC3 cells from the single experiment. FIG. 8B illustrated the transformed target Raman data 820 for normal PC3 cells from the single experiment. Note that in the single experiment, the transformed data from both the apoptotic PC3 cells 810 and normal PC3 cells 820 are on the left edge of the predetermined vector space for apoptotic PC3 cells 610 and normal PC3 cells 620. The "centroid" of a particular set of measurements may be defined as the mean weighted center of the points in a given plane. FIGS. 8A and 8B demonstrate that the centroid of the target Raman data sets 810 and 820 lies to the left of the centroid for the predetermined vector space of the apoptotic PC3 cells 610 and normal PC3 cells 620. The displacements in the centroids may result from the uncontrollable variables in the measurements.

Example 4

LnCAP cells, which like PC3 cells, are a prostate cancer cell line were also investigated. Apoptosis was induced in LnCAP cells following the same procedure as the PC3 cells of Example 1. As discussed for Example 1, reference Raman spectra were obtained from apoptotic and normal cells, and Principal Component analysis performed on the data to generate a classification model. FIG. 9 illustrates predetermined vector space for the normal (920) and apoptotic (910) LnCAP cells. Points labeled 910 mathematically describe the reference Raman data sets collected for apoptotic LnCAP cells. Points labeled 920 mathematically describe the reference Raman data sets collected for normal LnCAP cells. Similar to the PC3 cells, the LnCAP apoptotic and normal cells separate in principal component space. The axes of the scatter plot shown in FIG. 9 are not the same as the axes of the analogous scatter plots shown for PC3 cells in FIG. 6. This is because the classification model for LnCAP cells is different from the classification model for PC3 cells.

Example 5

PC3 cells were prepared as described in Example 1. The PC3 cells were then labeled with fluorescent tag, available through a commercial apoptosis detection kit, which allowed targeting of PC3 cells that not only had the characteristic shape, but expressed phosphatidylserine on the cell surface as indicated by annexin V-FITC labeling. FIG. 5B shows an example of such a treated PC3 cell. In general, fluorescence within a biological sample precludes the measurement of Raman scattered light as the molecules that comprise the samples undergo autofluorescence. It is a common observation that under the illumination of a strong light source, this autofluorescence dissipates with time through photobleaching. The fluorescently labeled cells were exposed to light in order to dissipate the luminescence. After the photobleaching process, it was possible to obtain high quality Raman spectra from the fluorescently labeled cells.

Figure 10B:
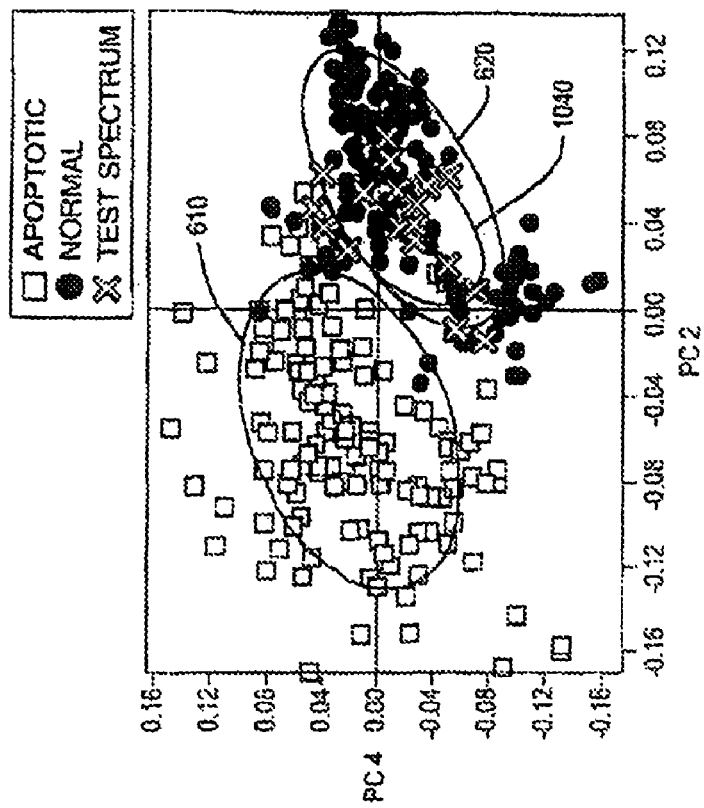
FIGS. 10A and 10B illustrate the projection of a Raman target data set for cells treated with fluorescent tags onto the vector space of the classification model for apoptotic and normal PC3 cells.
Figure 10A:
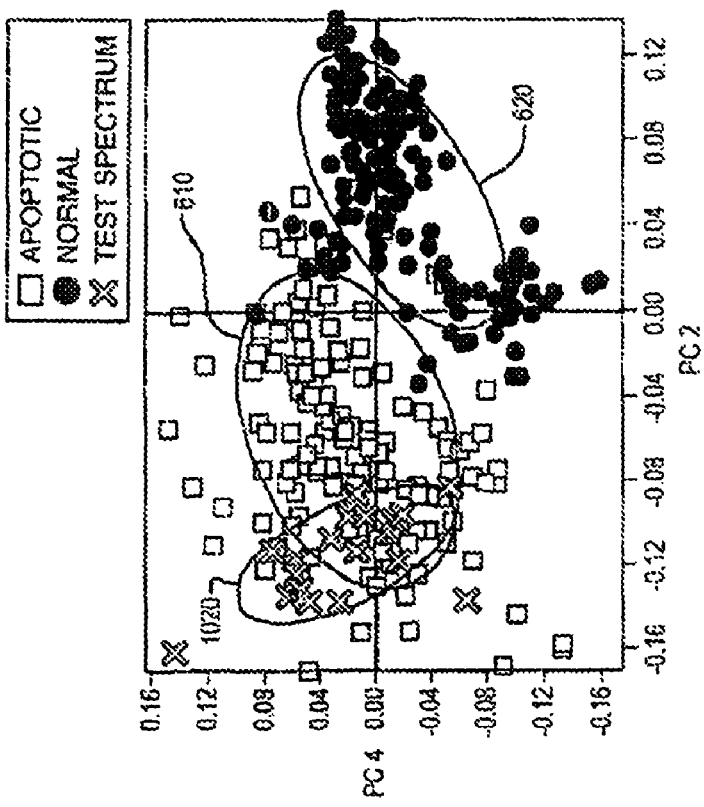

As an independent validation of the classification model described in Examples 1-4, target Raman data sets were collected and analyzed for PC3 cells that were positive for apoptosis based on the immunofluorescence labeling. Twenty cells that labeled positive for apoptosis with the fluorescent tag were photobleached. Target Raman spectra were then obtained as described in Example 1. In addition, the target Raman spectra of twenty cells that were negative according to the assay (did not label with the fluorescent tag) were acquired. The target Raman spectra of the PC3 cells were classified apoptotic or normal using the predetermined vector space for normal PC3 cells and apoptotic PC3 cells described in Example 1 and FIG. 6. The results are shown in FIGS. 10A and 10B. FIG. 10A shows X symbols (1020) indicating locations of the transformed target Raman spectra, of the fluorescence labeled PC3 cells, projected onto predetermined vector space. Groups of symbols 610 and 620 show the location of the original reference data in the vector space determined in example 1. The twenty cells which were apoptotic cells, based on fluorescently labeling all classified as apoptotic PC3 cells using the classification model of FIG. 6. FIG. 10B shows X symbols indicating the locations of the transformed target Raman spectra, of the unlabeled PC3 cells, projected onto predetermined vector space. Groups of symbols 610 and 620 show the location of the original reference data in the vector space determined in example 1. Using the classification model of FIG. 6, seventeen of the 20 normal cells, determined by fluorescence labeling, classified as normal PC3 cells using the classification model of the present disclosure.

The statistical results, shown in Table 2, demonstrate the classification results analyzing the fluorescence labeled and unlabeled PC3 cells.

|  | Apoptotic | Normal |
|---|---|---|
| Apoptotic | 20 | 3 |
| Normal | 0 | 17 |

The statistic analysis of the split data model showed a sensitivity of 100%, a specificity of 85.0%, a positive predictive value of 87.0% and a negative predictive value of 100.0%.

Example 6

The results discussed in Examples 1-5 are based on dispersive Raman spectral measurements of single cells. The illumination of the individual cell covers the entire area of the cell so the dispersive spectrum is an integrated measure of all the locations within the cell. Widefield spectral Raman imaging may also be used to evaluate apoptotic and normal cells. The advantage of widefield Raman spectrum imaging is that instead of a single spectral measurement of a cell, a spatially resolved spectral image provides spectral information about every micron of the cell at a given wavelength. In the imaging mode, there is a spectrum available that corresponds to each 0.5 by 0.5 micron region of the cell. This approach gives more statistical information, allowing characterization of samples where there is a mixture of normal and apoptotic cells, and will carry information about the subcellular molecular changes which occur with apoptosis.

Figure 11B:
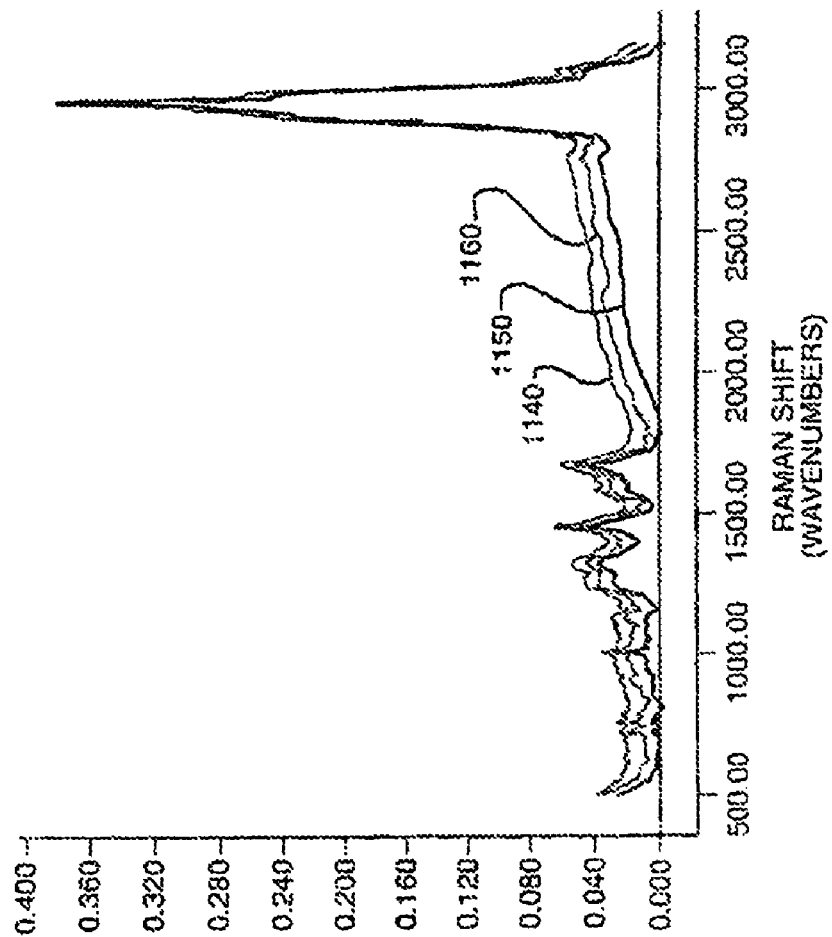
FIGS. 11A and 11B illustrate a Raman chemical image of normal and apoptotic PC3 cells and Raman spectra for regions of interest in the image.
Figure 11A:
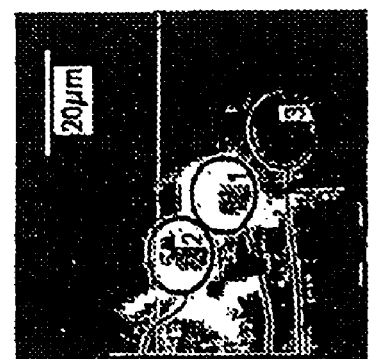

FIG. 11A shows a spatially accurate wavelength resolved Raman image of a mixture of normal and apoptotic cells at 2930 $cm^{-1}$. The image is made up of a plurality of pixels where each pixel has an associated Raman spectrum. FIG. 11B shows a series of Raman spectra obtained for regions of interest 1110, 1120 and 1130 in FIG. 11A. Spectrum 1140 corresponds to region of interest 1110. Spectrum 1150 corresponds to region of interest 1120. Spectrum 1160 corresponds to region of interest 1130. The spectra, of FIG. 11B, are the average of the collection of Raman spectra at each pixel within the particular region of interest.

Figure 12:
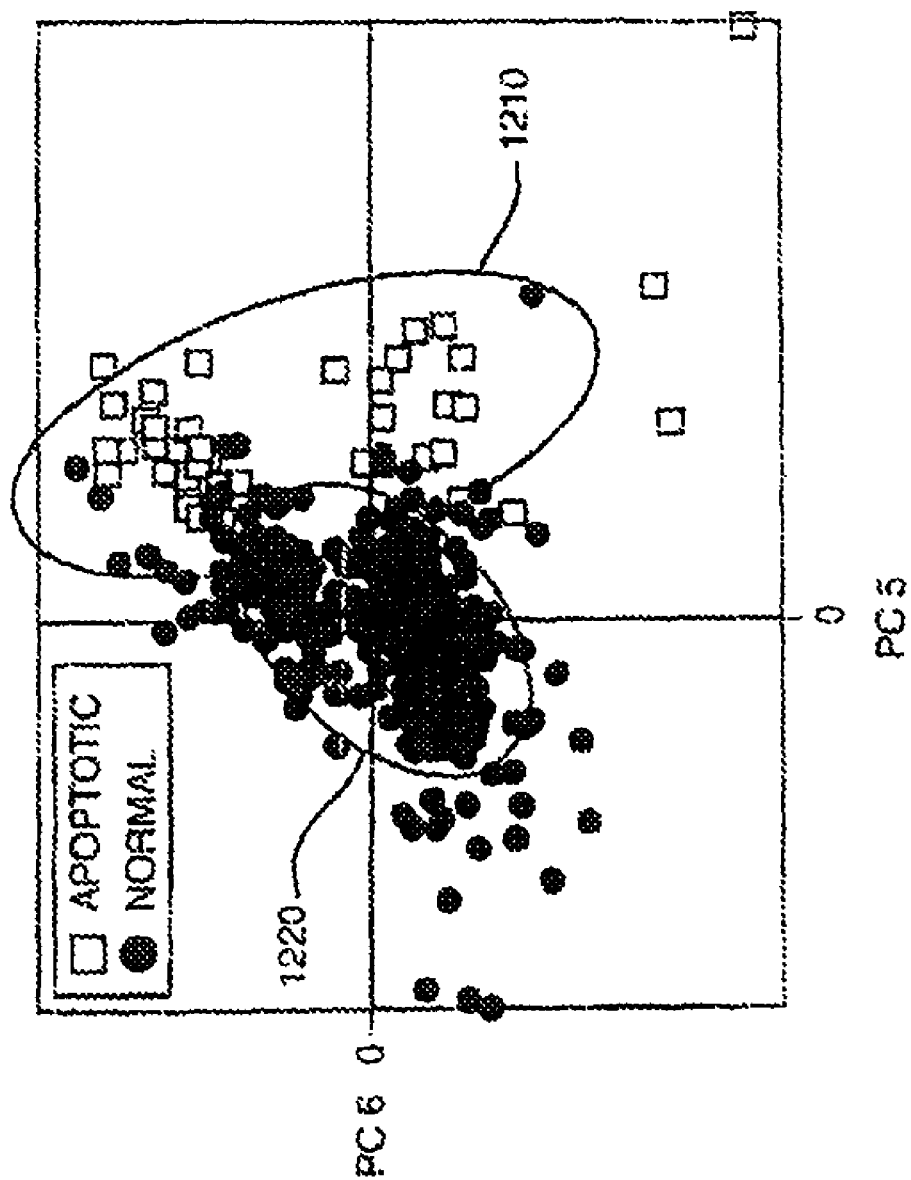
FIG. 12 illustrates projection of a Raman target data set, based on spatially accurate wavelength resolved Raman images, onto the vector space of the classification model for apoptotic and normal PC3 cells.

The Mahalanobis distance model approach was applied to the Raman reference dataset, a hypercube, using spectra extracted from a plurality wavelength resolved images. Regions of interest in the image were identified. The regions of interest contained apoptotic or normal cells based on size and shape of the cells using brightfield imaging or fluorescence tagging. From the regions of interest, Raman spectra were extracted from each pixel in regions of interest 1110, 1120 and 1140 as examples. The regions of interest may be smaller than the size of the cell under investigation. A reference Raman spectrum was generated for each pixel within the region of interest. To create the predetermined vector space for normal PC3 cells and apoptotic PC3 cells, two different reference Raman hypercubes were used. FIG. 12 shows a scatter plot of the normal and apoptotic spectral samples obtained from the Raman data set. FIG. 12 illustrates predetermined vector space with points indicating the apoptotic cells (1210) and normal cells (1220). The fact that the points 1210 representing the reference Raman spectra, for apoptotic PC3 cells, is on the right of the plot instead of the left (in contrast to FIG. 6, for example) is insignificant. The key point from FIG. 12 is that the reference Raman spectra, extracted from images of apoptotic and normal cells, are in distinct locations within the vector space determined by principal component analysis.

Figure 13:
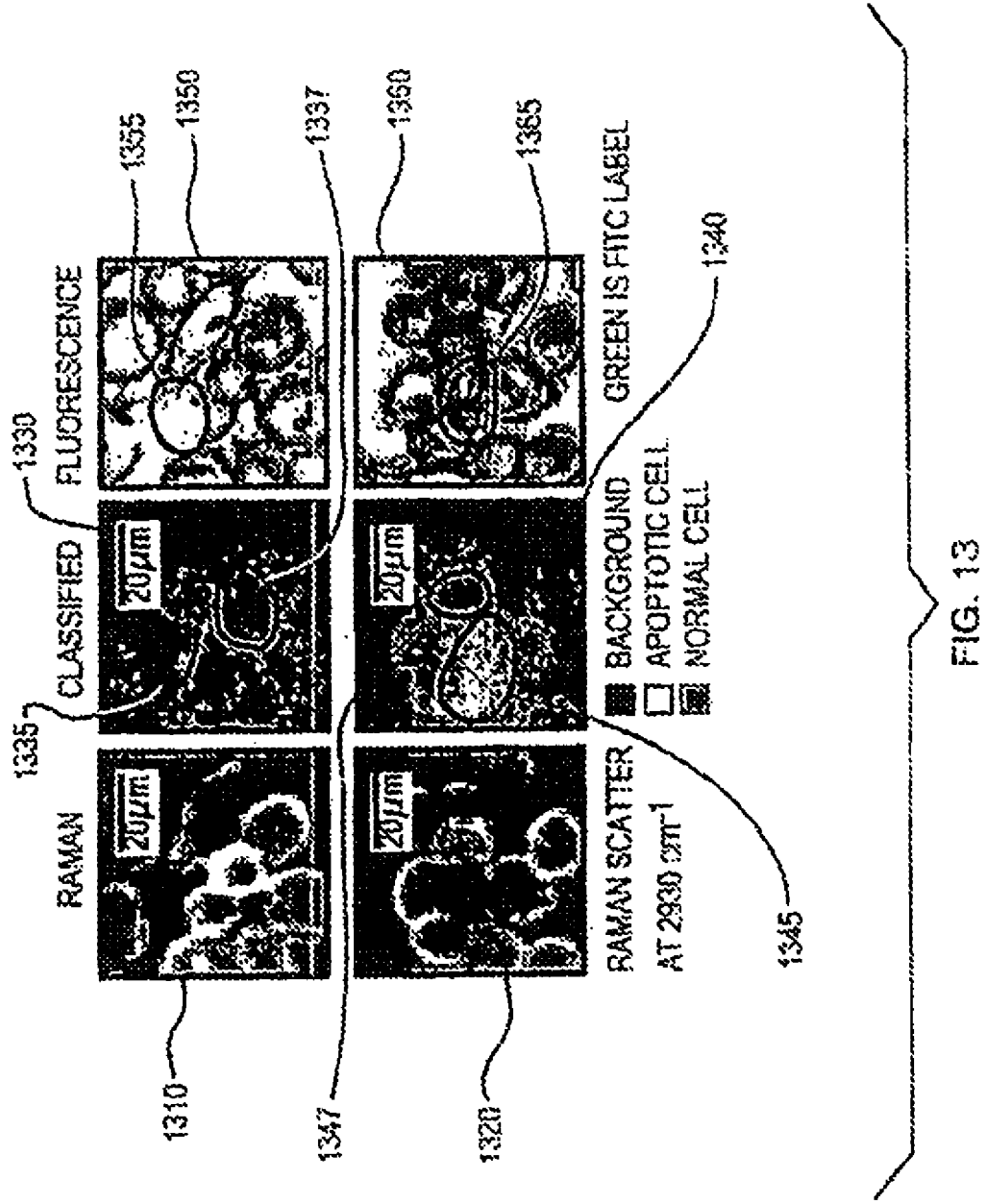
FIG. 13 illustrates Raman images, classification images and fluorescence images of two groups of cells.

The predetermined vector space was then used to classify each pixel in Raman images 1310 and 1320 shown in FIG. 13. The spatially accurate wavelength resolved Raman images of FIG. 13 were obtained at 2930 $cm^{-1}$. FIG. 13 also shows the Raman image-based classification of each pixel of the image in comparison to the fluorescence labeling with FITC. Fluorescence images 1350 and 1360 show images of normal and apoptotic PC3 cells labeled with FITC. Images 1350 and 1360 were taken in the same field of view as Raman images 1310 and 1320, respectively. Areas 1355 and 1365 are apoptotic cells as the cells exhibit fluorescence. Classification images 1330 and 1340 visually illustrate the areas classified as background area, apoptotic or normal cells. For example, area 1335 classified as containing apoptotic cells. Areas 1337 classified as containing normal cells. Area 1345 classified as containing apoptotic cells and area 1347 classified as containing normal cells. Ideally, areas for apoptotic cells in the classified image should overlay with the area for apoptotic cells in the fluorescently labeled cells. This is not completely the case. Reasons for disagreement include but are not limited to: 1) the signal to noise of the spectral image raw data which can add inaccuracy to classification, and 2) the difference between the spectral measurements. For example, FITC labels phosphatidylserine in the plasma membrane. The Raman measurement is not targeted based on a specific molecule, but rather the local molecular environment.

The present disclosure may be embodied in other specific forms without departing from the spirit or essential attributes of the disclosure. Accordingly, reference should be made to the appended claims, rather than the foregoing specification, as indicating the scope of the disclosure. Although the foregoing description is directed to the preferred embodiments of the disclosure, it is noted that other variations and modification will be apparent to those skilled in the art, and may be made without departing from the spirit or scope of the disclosure.

What is claimed is:
1. A method comprising:
    selecting a pre-determined vector space that mathematically describes a first plurality of reference spectral data sets for normal cells and a second plurality of reference spectral data sets for cells having undergone a biochemical change;

irradiating a sample containing at least one cell to thereby generate photons selected from the group consisting of: photons emitted from the sample, photons absorbed by the sample, photons reflected from the sample, photons scattered by the sample, and combinations thereof;

collecting said photons to thereby generate a target spectral data set;

transforming the target spectral data set into said pre-determined vector space;

analyzing a distribution of transformed data in the pre-determined vector space;

and based on said analysis, classifying at least one cell as a normal cell or a cell having undergone a biochemical change.

2. The method of claim 1 wherein said first reference data set of spectral data sets is selected from the group consisting of: a plurality of first reference Raman spectra wherein each spectrum corresponds to a reference normal cell, a plurality of first reference spatially accurate wavelength resolved Raman images wherein each image corresponds to a normal cell, a plurality of first reference infrared spectra wherein each spectrum corresponds to a reference normal cell, a plurality of first reference spatially accurate wavelength resolved infrared images wherein each image corresponds to a reference normal cell, a plurality of first reference ultraviolet spectra wherein each spectrum corresponds to a reference normal cell, a plurality of first reference spatially accurate wavelength resolved ultraviolet images wherein each image corresponds to a reference normal cell, a plurality of first reference visible spectra wherein each spectrum corresponds to a reference normal cell, a plurality of first reference spatially accurate wavelength resolved visible images wherein each image corresponds to a reference normal cell, and combinations thereof.

3. The method of claim 1 wherein said target spectral data is selected from the group consisting of: a plurality of Raman spectra of the sample, a plurality of spatially accurate wavelength resolved Raman images of the sample, a plurality of infrared spectra of the sample, a plurality of spatially accurate wavelength resolved infrared images of the sample, a plurality of ultraviolet spectra of the sample, a plurality of spatially accurate wavelength resolved ultraviolet images of the sample, a plurality of visible spectra of the sample, a plurality of spatially accurate wavelength resolved visible images of the sample, and combinations thereof.

4. The method of claim 1 wherein said photons are collected via a fiber array spectral translator device.

5. The method of claim 1 further comprising passing said photons through a liquid crystal tunable filter.

6. A method comprising:
selecting a pre-determined vector space that mathematically describes a first plurality of reference spectral data sets for normal cells and a second plurality of reference spectral data sets for cells having undergone a biochemical change;
treating a sample with a pharmaceutical agent;
irradiating the sample containing at least one cell to thereby generate photons selected from the group consisting of: photons emitted from the sample, photons absorbed by the sample, photons reflected from the sample, photons scattered by the sample, and combinations thereof;
collecting said photons to thereby generate a target spectral data set;
transforming the target spectral data set into said pre-determined vector space;
analyzing a distribution of transformed data in the pre-determined vector space;
and based on said analysis, classifying at least one cell as a normal cell or a cell having undergone a biochemical change; and
based on said classifying, assessing a therapeutic efficiency of said pharmaceutical agent.

7. The method of claim 6 wherein said treatment results in one of the following: causing a biological change in at least one cell in said sample and preventing a biological change in at least one cell in said sample.

8. The method of claim 7 wherein said biological change comprises apoptosis.

9. A method comprising:
selecting a pre-determined vector space that mathematically describes a first plurality of reference spectral data sets for normal cells and a second plurality of reference spectral data sets for cells having undergone a biochemical change;
irradiating a sample containing at least one cell to thereby generate photons selected from the group consisting of photons emitted from the sample, photons absorbed by the sample, photons reflected from the sample, photons scattered by the sample, and combinations thereof;
collecting said photons to thereby generate a target spectral data set;
transforming the target spectral data set into said pre-determined vector space;
analyzing a distribution of transformed data in the pre-determined vector space by calculating a Mahalanobis distance between the target spectral data set transformed into vector space and one or more of the following: a first plurality of reference spectral data sets in said pre-determined vector space; and a second plurality of reference spectral data sets in said pre-determined vector space; and
based on said analysis, classifying at least one cell as a normal cell or a cell having undergone a biochemical change.

10. A system comprising:
a first data base having a first plurality of reference spectral data sets representative of normal cells;
a second data base having a second plurality of reference spectral data sets representative of cells having undergone a biochemical change;
an illumination source;
a spectroscopic device;
a machine readable program code containing executable program instructions; and
a processor operatively coupled to the illumination source and the spectroscopic device, and configured to execute said machine readable program code so as to perform the following:
select a pre-determined vector space that mathematically describes the first plurality of reference spectral data sets representative of normal cells and the second plurality of reference spectral data sets representative of cells having undergone a biochemical change,
configure said illumination source to illuminate a biological sample with light to thereby generate photons selected from the group consisting of: photons emitted from the sample, photons reflected by the sample, photons absorbed by the sample, photons scattered by the sample, and combinations thereof;
configure said spectroscopic device to collect a spectral data set based on said photons selected from the group consisting of: photons emitted from the sample, photons reflected by the sample, photons absorbed by the sample, photons scattered by the sample, and combinations thereof;

transform the target Raman data set into a vector space defined by the pre-determined vector space;

analyze a distribution of transformed data in the predetermined vector space;

based on said analysis, classify the biological sample as comprised of one of the following: normal cells, cells having undergone a biochemical change, and combinations thereof.

11. The system of claim 10 further comprising a fiber array spectral translator.

12. The system of claim 10 further comprising a liquid crystal tunable filter.

13. The system of claim 12 further comprising a fiber array spectral translator.

\* \* \* \* \*